United States Patent [19]
Jorgensen

[11] Patent Number: 5,180,873
[45] Date of Patent: Jan. 19, 1993

[54] TRANSFORMATION OF PLANTS TO INTRODUCE CLOSELY LINKED MARKERS

[75] Inventor: Richard A. Jorgensen, Berkeley, Calif.

[73] Assignee: DNA Plant Technology Corporation, Oakland, Calif.

[21] Appl. No.: 723,857

[22] Filed: Apr. 16, 1985

[51] Int. Cl.⁵ .................. A01H 1/04; A01H 1/00; C12N 15/00; C12N 9/00; C12P 21/00

[52] U.S. Cl. ................. 800/205; 435/172.3; 435/69.1; 435/183; 47/58; 47/DIG. 1; 935/64; 935/67

[58] Field of Search ............ 435/172.3, 317, 240, 435/241, 317, 948; 935/52, 67; 47/58, DIG. 1; 800/1, 205, 69.1, 183

[56] References Cited

U.S. PATENT DOCUMENTS

| | | | |
|---|---|---|---|
| 2,753,663 | 7/1956 | Jones | 47/58 |
| 3,710,511 | 1/1973 | Pattterson | 47/58 |
| 3,861,079 | 1/1975 | Patterson | 47/58 |
| 4,051,629 | 10/1977 | Galinat | 47/58 |

FOREIGN PATENT DOCUMENTS

| | | |
|---|---|---|
| 122791 | 10/1984 | European Pat. Off. |
| 2464641 | 3/1981 | France |
| 2139466 | 11/1984 | United Kingdom |

OTHER PUBLICATIONS

Vrsic et al., 1983 Mol. Gen. Genet. 190 494–503.
Goodman et al., 1987 Science 236:48–54.
De Block et al., 1984 EMBO J 3(8):1681–1689.
Horsch et al., 1984 Science 223:496–498.
Helmer et al., 1984, Biotechnology, June: 520–527.
Inzé et al., 1984 Mol. Gen. Genet. 194:265–274.
Ensley et al., 1983 Science 222:167–169.
Owens, L. D. 1973 Weed Sci. 21:63–66.
Bevan et al., 1983 Nature 304:184–187.
De Framond et al., 1986, Biol. Abstr. #85840 vol. 81 No. 9 Pandey, K. K. 1980 Biol. Abstr. 71(6): Abstr #38353.
Matzke et al., 1981 Biol. Abstr. 74(7): #46777.
Koziel et al., 1985 Biol. Abstr. 79(10): #89649.
Hoekema et al., 1985 Biol. Abstr. 81(1) #4045.
Waldron et al., 1985 Biol. Abstr. 81(1): #4046.
Wallroth et al., 1986 Biol. Abstr. 81(11):#101682.
Frankel et al., 1977 Pollination mechanisms, reproduction and plant breeding, Springer-Verlag, §3.4.1.2. and 3.4.2.1 and 3.4.4.
Singleton et al., 1930 J. Heredity 21: 266–268.
Yardanov, M. 1983, Monographs on Theor. and Appl. genetics 6:189–219.
Foster, C. A. Barley Genetics III: 774–784. 1976.
Foster, C. A. 1979, Barley genetics newsletter 9:22–23.
Tanksley, S. D. 1983, Plant molecular biologyreporter 1:3–8.
Gottschalk et al., 1983 Monographs on Theoretical and applied genetics, "induced mutations in plant breeding", 7–70.
Welsch, J. R. 1981 Fundamentals of Plant genetics and breeding Ch. 16, 18. John Wiley and Sons.
Wiebe, G. A. 1960, Agren. J. 52:181–182.
Wiebe, G. A. 1964 Barley Newsletter 8:16.
Ramage, R. J. 1966, Barley newsletter 9:3–8.
Philouze, J. 1974, Ann. Amel. Plant 24:77–82.
Ramage, R. T. 1983 Managraphs on Theoretical and applied genetics 6:71–93.
Driscell, C. J. 1972. Crys. Sci. 12:516–517.
Wilson et al., 1983 Hybrid wheat pp. 94–123 *In Monographs on theoretical and applied genetics.*
Syberga, J. 1983 Theor. Appl. Genet 66:179–201.
Falk et al., 1981 Barley genetics IV: 778–785.
Rick et al., 1983 Isozymes: Current Topics in Biological and Medical Research 11:269–284.
L. Otten et al., *Mol. Gen. Genet.*, 183, 209–213 (1981).
Chem. Ab. 62584, vol. 100, 1984 (Schroeder).
Chem. Ab. 85227, vol. 103, 1985 (Matthews).
R. B. Horsch et al., *Science*, 227, 1229–1231 (1985).

*Primary Examiner*—David T. Fox
*Attorney, Agent, or Firm*—Clinton H. Neagley

[57] ABSTRACT

A novel method of producing a plant with a marker closely linked to a target locus, in particular a nuclear male sterile target locus, is described. The method involves transformation of a group of plants in order to introduce a marker into each plant, and isolation of a plant with the marker closely linked to a target locus. The markers include visible markers and dominant conditional lethal markers. The method is of particular use for hybrid seed production where the target locus is a nuclear male sterile locus.

39 Claims, 4 Drawing Sheets

TRANSFORMATION OF PLANTS TO INTRODUCE CLOSELY LINKED MARKERS

FIELD OF INVENTION

This invention relates to a method of producing a plant with a marker closely linked to a target locus, in particular a nuclear male sterile target locus. This invention more particularly relates to transformation of a group of plants in order to introduce a marker into each plant, and isolation of a plant with the marker closely linked to the target locus. The invention is of particular use for hybrid seed production where the target locus is a nuclear male sterile locus.

BACKGROUND OF THE INVENTION

The use of hybrid plants in agricultural crops is well known as a means to enhance plant production and value. A hybrid plant is one resulting from a crossing (an outcrossing) other than a self-crossing (selfing) or a sibling-crossing (sibbing), in particular between inbred lines. Hybrid crossing, or hybridization, is commonly accomplished by having side by side stands or rows ("crossing" rows), with female stands (P1) alternating with pollinating rows (P2). Pollen is normally carried by insects or wind, although in some commercial plants pollination is by hand.

The value of the hybrid is primarily in the increased yield and vigor, or heterosis, which is displayed as compared to the parents, in particular in the first generation (F1) of progeny. Selfing of a hybrid (F1) results in a second generation of plants (F2) which normally exhibits less heterosis than is displayed by the F1 generation. Hybrids have been commercially used in a great variety of plants and crops, including wheat, field corn, sweet corn, barley, sorghum, sugar beets, garden beets, onions, tomatoes, cabbage, cauliflower, broccoli, brussels sprouts, cucumber, carrot, spinach, summer and winter squash, asparagus, pepper, eggplant, radish, muskmelon, watermelon, pumpkin, cantaloupe, tobacco and various ornamentals.

In developing hybrid seed (i.e., seed from which the first generation hybrid is to be grown), the ability to control mass pollination is important. Specifically, prevention of parental selfing or sibbing, which would result in the production of non-hybrid seed, is important. Several methods have been used, or considered, for ensuring or maximizing hybridization.

One method is to emasculate the female parent line (P1), either by hand or mechanically. For instance, in the alternating stand situation, if the P1 stand is emasculated, plants in that stand can only be pollinated by plants from another stand, i.e., the pollinating stand. While this has been done with some plants, e.g., tomato (manual) and corn (manual and mechanical), manual emasculation is labor intensive and impractical for volume crops, and mechanical emasculation cannot be used for many crops and can cause yields to suffer due to plant damage.

A second method is the use of chemical agents (gametocides) to emasculate the intended female parents. Although attempts have been made to develop such chemicals, the approach has a number of problems. The chemical must provide sufficient male sterility without otherwise affecting the plant. There is the need to treat selectively only the ultimate female parents and to spray only in the proper amounts. Plants sprayed with insufficient chemical or sprayed at the wrong stage of development may not be rendered male sterile (so-called "shedders"). In addition, the cost of the gametocide may be a factor.

A third method applies to those plants in which cytoplasmic male sterility (cms) has been found, e.g., cotton, tobacco, rice, corn, onions, sorghum, carrot, radish, alfalfa and certain flowers and grasses. For such plants, cms in the female parent will ensure its outcrossing. The approach is limited in that, in general, the occurrence of cms in crops is rare. Also, for those crops in which the product depends on fertilization the use of cms is workable only if a restorer gene is available for the particular plant to permit restoration of fertility of the F1 hybrid. In addition, cms is often associated with undesirable traits, some of which may not appear at the outset. For instance, a cms system used in maize led to the Southern leaf blight epidemic of the early 1970's. U.S. Pat. No. 2,753,663 discloses the use of cms in corn.

A fourth method which has been considered is the use of nuclear male sterility, also referred to as chromosomal or genic male sterility. Nuclear male sterile genes presumably result from a mutation at some point in the development of a plant or its ancestors. The genes occur in practically all diploid plant species which have been examined for this property, and are present as well in polyploid plants. The genes are normally recessive. Nuclear male sterile genes have been studied in a large number of plants of agricultural interest, e.g., wheat, corn, tomato, barley, pepper, rice, lima beans, peas, cotton, watermelon, soybeans, tobacco, lettuce and various ornamentals.

See R. Frankel et al., *Pollination Mechanisms, Reproduction and Plant Breeding*, (Springer Verlag), 3.4.1.2 and 3.4.2.1 (1977) See W. Gottschalk et al., *"Induced Mutations in Plant Breeding", Monographs on Theoretical and Applied Genetics*, 7, 70 (Table 13) (1983) for a list of induced male sterile mutants in cereals and dicotyledonous plants. For many plants there are a number of male sterile loci, each of which can have either a recessive male sterile (ms) or a dominant male fertile (Ms) allele. For a diploid plant, such a locus (allele pair) can be homozygous male sterile (ms/ms), homozygous male fertile (Ms/Ms), or heterozygous male fertile (Ms/ms). The nomenclature shown is for recessive male sterility. In the less likely instance of dominant male sterility, the nomenclature would be the opposite (Ms male sterile; ms male fertile). Unless otherwise stated, the nomenclature used herein is for recessive male sterility. Nuclear male sterility and nuclear male sterile plant, line, gene, locus, etc. shall on occasion be referred to herein, respectively, as male sterility and male sterile plant, line, gene, locus, etc.

Nuclear male sterility has use in hybrid breeding in that if the female parent displays nuclear male sterility (e.g., in a diploid plant, if the plant is homozygous for recessive ms), the female parent cannot function as a male parent and seeds obtained from it by outcrossing are necessarily hybrid seeds. In the alternating stand situation, nuclear male sterile female stands alternate with pollinating stands. Seed harvested from the female stands can be used as hybrid seed.

The use of nuclear male sterility in hybrid breeding requires a means to maintain the nuclear male sterile line. Since male steriles produce no pollen, to be maintained they must be produced anew each generation from segregating progenies. For a diploid plant, a maintainer line is typically obtained by crossing the male sterile line (ms/ms) with a male fertile line (Ms/Ms). The product is a heterozygous maintainer line (Ms/ms) which is used to generate the next generation male sterile line in a crossing to a homozygous male sterile line (ms/ms). The progeny of this crossing are 50% homozygous male sterile (ms/ms) and 50% heterozygotes (Ms/ms). In such a situation there must be a means to isolate the male sterile plants for use as the female parent in hybrid breeding. This has to a large extent been done by visual inspection, although there have been suggestions for using either natural linkage or chromosomal abnormalities to assist in isolating male steriles. See, in general, J. R. Welsh, *Fundamentals of Plant Genetics and Breeding*, Chaps. 16, 18 John Wiley and Sons, (1981) for a discussion of hybrid breeding and male sterility systems.

The visual inspection approach to isolating male steriles involves examining individual plants in the field at the time of anthesis. Male fertiles often show physical differences, e.g., in anther structure, which permit them to be mechanically or manually removed (rogued). While this approach has been used for some crops, it is not effective for many plants of agronomic interest. Moreover, it is labor intensive and cannot be used for selection at an early stage of plant development.

Another approach to obtaining male sterile stands involves the use of naturally occurring linkage. As used herein, the term linkage means genetic linkage between two or more loci (or genes) in a given genome such that the recombination frequency between the loci (or genes) is less than 50%, the frequency of random assortment. As so used, the term usually refers to loci (or genes) in sufficiently close proximity on the same chromosome of a given plant that recombination between them occurs less frequently than if the genes were located on separate chromosomes. The term, as used herein, also embraces other forms of genetic linkage where the recombination frequency deviates from random assortment. The extent of linkage is measured in terms of the recombination frequency, or recombination units. Linked genes are normally transmitted or inherited together at a frequency related to their recombination frequency, as can be shown by segregation analysis of progeny resulting from a crossing. If a chromosomal recombination (a crossover or other rearrangement event) takes place, linked alleles may not be transmitted together. The tighter the linkage, the less likely is a recombination resulting in disruption of the linkage. For instance, very tight linkage exists if the linked genes are adjacent to each other on the same chromosome. As stated, the extent of linkage is measured in terms of recombination units. If two genes are separated by ten recombination units, there is a 10% chance of their becoming uncoupled in a crossing. A separation of five recombination units constitutes a tighter linkage.

There have been a number of proposals for using naturally occurring linkages between a male sterile gene and a marker gene (i.e., linkages, involving male sterile mutants, either discovered in nature or resulting from a breeding program) as a means of detecting or isolating male sterile plants or seeds from a mixture of male steriles and male fertiles. There is a 1930 disclosure of the possibility of using naturally occurring linkage between nuclear male sterility and seed color in bicolor corn in a program to produce hybrid corn seed; W. R. Singleton et al., *Journal of Heredity*, 21, 266–68 (1930). Other disclosures concern the use of natural linkage in barley between male sterility and recessive DDT resistance as a means of removing male fertiles (upon application of DDT) in a hybrid program; G. A. Wiebe, *Argon. J.*, 52, 181-82 (1960) and G. A. Weibe, *Barley Newsletter*, 8, 16 (1964). Wiebe (1964) also discloses the possibility of reducing the crossover value (that is, tightening the linkage) either by using radiation to invert chromosomal segments or by breeding for translocations. Use of linkage between a male sterility gene and a gene for non-germination upon treatment of a particular chemical is suggested in R. T. Ramage, *Barley Newsletter*, 9, 3–8 (1966). Linkage between male sterility and color, or lack-of-color, genes is disclosed in J. Philouze, *Ann. Amel. Plant.*, 24, 77–82 (1974), cited in M. Yardanov, *Monographs on Theoretical and Applied Genetics*, 6, 189–219 (1983). Such linkage is also disclosed in C. A. Foster, *Barley Genetics Newsletter*, 9, 22–23 (1979). Linkage between a male sterile locus and a shrunken seed gene is disclosed in D. E. Falk et al., *Barley Genetics*, IV, 778–85 (1981). A tomato mutant with linkage between an isozyme marker and a male sterile locus resulting from a breeding program is disclosed in S. D. Tanksley, *Plant Molecular Biology Reporter*, 1, 3–8 (1983) and C. M. Rick et al., *Isozymes: Current Topics in Biological and Medical Research*, 1, 269–84 (1983). Natural linkage is also disclosed in C. A. Foster, *Barley Genetics*, III, 774–84 (1976); and R. T. Ramage, *Monographs on Theoretical and Applied Genetics*, 6, 71–93 (1983). The marker is termed a "haplo-viable" mutation (Ramage, at 84); it is linked to the dominant allele of the male sterile locus. So-called haplo-viable mutations can be transmitted through the egg but not through the pollen. The use of natural linkage to assist in isolating male steriles is limited by the lack of appropriate markers for many crops of agricultural interest and also, for those crops for which markers are known, by the lack of sufficient closeness of linkage.

Another approach for obtaining male sterile lines which has been suggested involves the use of chromosomal abnormalities. One type of abnormality is a differentially transmitted chromosome, e.g., a duplicate deficient chromosome (egg-viable but not transmitted by pollen) as disclosed in U.S. Pat. No. 3,710,511. This chromosomal variation is disclosed as occurring naturally or resulting from mutagenic agents. If a female stand is produced from a Ms/ms heterozygote in which the male fertile allele is linked with a differentially transmitted chromosome (transmitted through the female parent but not the male parent), selfing or sibbing can be avoided. Another type of chromosomal abnormality is the presence of an extra chromosome, meaning the presence of an additional chromosome from the same species or the presence of an additional chromosome from a related species. R. T. Ramage, *Barley Newsletter*, 9, 3–8 (1966) discloses a system in barley with an extra chromosome (a trisomic system) resulting from disjunction during mitosis. The extra chromosome is transmitted through the female germ line but only rarely transmitted through the male. Fertility genes and marker genes (e.g., phytocide susceptibility, height, seed size or shape) on the extra chromosome permit production and identification of male sterile female parents. C. J. Driscoll, *Crop Sci.*, 12, 516–17 (1972) discloses an analogous system for hybrid wheat using an extra chromosome derived from rye. U.S. Pat. No. 4,051,629 also discloses an extra chromosome system. In addition, systems with extra chromosomes are disclosed in R. Frankel et al., *Pollination Mechanisms, Reproduction, and Plant Breeding*, (Springer Verlag), §3.4.4

(1977); P. Wilson et al., "Hybrid Wheat", *Monographs on Theoretical and Applied Genetics*, Chap. 4, 94–123 (1983); and J. Sybenga, *Theor. Appl. Genet.*, 66, 179–201 (1983). Sybenga, at 194, suggests the further development of an extra ("alien") chromosome system by constructing such a chromosome using molecular genetic engineering. In general, the extra chromosome approach is limited (a) by difficulties in deriving the appropriate system, as well as (b) by problems of low pollen yield.

SUMMARY OF THE INVENTION

In accordance with the invention, a method is provided for producing a novel plant with a marker gene (marker) closely linked to a target locus, in particular where the target locus is a male sterile locus. A marker closely linked in this manner shall be referred to herein on occasion as a close-linkage marker and a plant so produced, or progeny of such a plant, shall be referred to as a close-linkage plant. The novel plant is obtained by transforming a first plant with a marker using genetic engineering techniques to produce a group of transformed plants (transformants) containing the marker at various positions within the plant genome of different transformants. Selection is made for transformants containing the introduced marker at a single locus within the transformant (i.e., single locus transformants). The selection for single locus transformants is preferably accomplished by conducting crossings, either self-crossings or outcrossings (for instance, outcrossing with homozygous male sterile plants), of each transformant, and scoring (analyzing or testing) the progeny of the crossings for presence of marker to determine, based on segregation patterns, whether a given transformant is a single locus transformant. Multiple locus transformants (transformants other than single locus transformants) are either discarded or converted to single locus transformants by further crossing and progeny testing. From the group of single locus transformants, selection is made for those plants containing the marker in close or tight linkage with the target locus. Where the target locus is a male sterile locus, the marker can be linked either to the male sterile allele or the male fertile allele, as long as it is linkage in coupling phase (dominant alleles of marker and male sterile loci on same chromosome). If the linkage is in repulsion rather than in coupling phase, the phase can be reversed by a separate recombination crossing step.

The selection for close-linkage plants is made by conducting crossings of each single locus transformant (e.g., for a male sterile target locus, crossings with homozygous male sterile plants followed by selfing or backcrossing of the hybrid), and by scoring the progeny to determine, based on the segregation pattern, whether the marker is closely linked to the target locus. The greater the association between the marker and the target locus in the segregation distribution, the closer the linkage.

Where the target locus is a male sterile locus, a male sterile gene can be present at the time of transformation or it can be subsequently introduced by crossing of the transformant and selection (from the first or second generation of progeny) of a plant containing the male sterile gene in the desired form (e.g., heterozygous). The first plant (the plant to be transformed) can be homozygous male sterile, homozygous male fertile, or heterozygous.

Transformation of a plant can be carried out using various methods. A preferred method is the use of the natural vector system Agrobacterium (including both *Agrobacterium tumefaciens* and *Agrobacterium rhizogenes*), for instance by cocultivation or inoculation techniques. An especially preferred method is transformation using *Agrobacterium tumefaciens* containing Ti plasmid vectors, where the vectors contain the marker within the T region but the tumor-causing genes are removed or inactivated (i.e., the vector is disarmed). Transformation using transposons can also be used. In addition, transformation may be by take-up of naked DNA. Transformed plants can be regenerated using known techniques. The method of the invention can be used with plants amenable to transformation and regeneration techniques. The invention embraces novel close-linkage plants, or seeds, produced by this method.

Markers for use with the invention can be either expressive markers or conditional expressive markers. Expressive markers include visible markers and assayable markers. Conditional expressive markers include conditional color markers (chromogenic markers), conditional resistance markers (e.g., antibiotic resistance or herbicide resistance), and dominant conditional lethal markers. When closely linked to a male sterile locus, these markers permit detection of male sterility, either directly or conditionally upon application of a chemical, preferably at an early stage of plant development, i.e., at a stage before anthesis, and most preferably at the seed or seedling stage. The invention embraces plants transformed with these markers.

In accordance with the invention, close linkage between marker and a target locus can be generated at various levels of closeness, depending on the number of transformants and the number of crossings involved in selecting a close-linkage plant. Depending on the intended use of the close-linkage plant, linkages of about 20 units can be useful. In general, and particularly where the target locus is a male sterile locus, the linkage is preferably less than about 10 units, with linkages of less than about 5, 3, or 1 unit, respectively, being increasingly preferred.

In accordance with the invention the means is provided to create close linkage between a marker gene and a target locus in a wide variety of plants, including those for which such linkage was not previously known in nature. The invention is of particular use for plants which reproduce by seed (i.e., sexually reproducible plants). The invention provides the means to create linkage at levels of closeness of use as a general breeding tool, e.g., to survey for male sterile parents. In particular, the invention is of use in hybrid breeding as a means to isolate and separate male sterile plants for use as female parents. Through use of the invention pure or substantially pure rows of male sterile plants can be produced for use as female parents in production of substantially pure hybrid seed.

Where the close-linkage plants are used in hybrid breeding, the close-linkage plant is preferably used as, or converted to by crossing, a maintainer line heterozygous for male fertility and heterozygous for the marker. The maintainer line can be crossed with a homozygous male sterile line to yield a 50:50 mixture of male fertile and male sterile plants. The male fertiles are removed from the mixture based upon the presence of the marker. If the marker is an expressive marker, the fertiles are removed based on presence or absence of color. If the marker is a conditional expressive marker, all the plants in the mixture are subjected to the applicable chemical and fertiles are removed based on the appearance, or lack of appearance, of color (if the marker is a chromogenic marker); slight plant damage (if the marker is a resistance marker); or lethality (if the marker is a dominant conditional lethal marker). With male fertiles removed, the remaining substantially pure group of male steriles can be used as the female plants in hybrid crossing The female plants are pollinated with pollen from an inbred line and hybrid seed is harvested for sale or planting. The maintainer line can be maintained indefinitely by backcrossing and selection of maintainer progeny.

DETAILED DESCRIPTION

Figure 1:
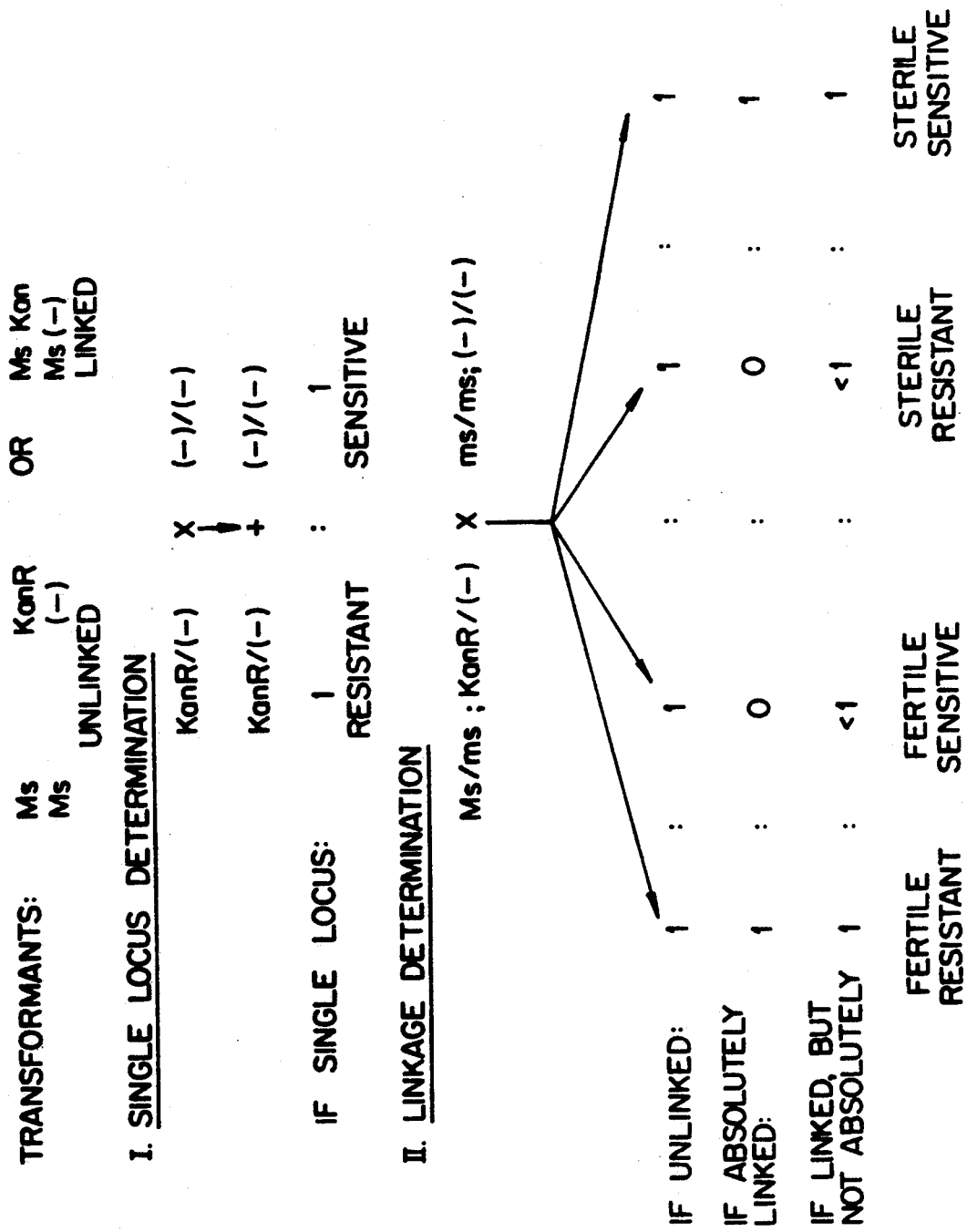
FIG. 1 is a depiction of steps involved in selection of plants made in accordance with the invention.

The invention comprises a method of producing novel plants, the novel plants so produced, and methods of using the novel plants. As used herein, the term plant means either a whole plant, a plant part, a plant cell, or a group of plant cells. The class of plants which can be used in the method of the invention is as broad as the class of higher plants amenable to transformation techniques. It includes plants of a variety of ploidy levels, preferably diploid. Polyploids best lend themselves to use in the invention if they are functional diploids, e.g., for a tetraploid, if there are two chromosome pairs with one pair homozygous ms/ms and the other pair heterozygous Ms/ms. The class of plants also includes plants which contain one or more target loci or in which target loci can be introduced. The invention has particular application to plants which benefit, or stand to benefit, from hybrid breeding techniques.

The invention is further described with particular reference to male sterile loci as the target loci, e.g., for use in hybrid breeding, but with the understanding that other target loci could be employed. For instance, in plant breeding, the locus could be any locus of interest (e.g., disease resistance) which the breeder desires to follow by the presence of close-linkage markers. Close-linkage plants for use in hybrid breeding are of importance for plants of agricultural interest, including dicotyledenous plants such as tomato, tobacco, cotton, rapeseed, field beans, soybeans, peppers, lettuce, peas, alfalfa, clover, cole crops or Brassica oleracea (e.g., cabbage, broccoli, cauliflower, brussels sprouts), radish, carrot, beets, eggplant, spinach, cucumber, squash, melons, cantaloupe, sunflowers and various ornamentals, and monocotyledenous plants such as asparagus, field or sweet corn, barley, wheat, rice, sorghum, onion, pearl millet, rye and oats.

The invention may be used with plants which have a target locus, e.g., a male sterility locus, which is found to exist in nature, which is introduced by mutagenesis, which is introduced to the plant through breeding, or which is otherwise introduced. In nature, male sterility occurs spontaneously in many field plants at a frequency of 1 in $10^4$ to 1 in $10^5$, and thus is easy to isolate. Techniques of mutagenesis can yield frequencies on the order of 1 in $10^3$. There can be a single male sterile locus or multiple loci. If there are more than one male sterile loci, the phrase heterozygous for male fertility means heterozygous for at least one of the loci.

Many plants have been studied genetically in detail and information is available about male sterile loci and their positions. In tomato, a well studied species, there are over thirty known male sterile genes; in corn there are approximately fifteen, in barley over twenty, and in sorghum six. Male sterile genes have also been studied in rice, cotton, pea, soybean, tobacco, pepper, eggplant and lettuce. Male sterile lines of these plants are available.

As stated, male sterility is normally recessive, and thus is not expressed unless the plant is homozygous ms/ms. The method of the invention has particular application for plants with such recessive male sterile alleles. The method can also be used, however, for dominant male sterile alleles in crops where seed is not an important product, e.g., spinach, cabbage, lettuce, broccoli, cauliflower and brussels sprouts.

The transformation of plants in accordance with the invention may be carried out in various ways known to those skilled in the art of plant molecular biology. As used herein, the term transformation means alteration of the genotype of a host plant by the introduction of foreign DNA such that it is integrated into the genome. The term transformable plant, as used herein, means a plant which can be transformed. Normally, regeneration will be involved in obtaining a whole plant from the transformation process. The term regeneration, as used herein, means growing a whole plant from a plant cell, a group of plant cells, a plant part or a plant piece (e.g., from protoplast, callus, or tissue part).

As used herein, the term marker refers to a gene (or group of two or more genes) conditioning, or encoding, a trait (or a phenotype) which permits the selection of, or the screening for, a plant containing the marker. There are two categories of markers of use with the invention: expressive markers and conditional expressive markers.

Expressive markers are markers which are expressed without chemical treatment, with the expression product either being directly observable, or assayable. One type of expressive marker is a visible marker, i.e., a marker for a visible trait such as color, fluorescence or plant morphology. Such a marker can be visible throughout the plant, or localized on a particular plant part, e.g., leaf, stem, flower, endosperm, cotyledon or aleurone (seed). A visible marker of choice is a color marker, preferably one which is identifiable before pollen release (anthesis), e.g., at the seed or seedling stage. A visible marker can be either dominant or recessive. If the visible marker is dominant, it is linked in coupling with the dominant male fertile allele (where the target locus is a male sterile locus); if recessive, it is linked in coupling with the recessive male sterile allele.

An example of an expressive marker which is a visible marker is the gene for naphthalene dioxygenase, an enzyme which converts indole into the pigment indigo. The enzyme is encoded for by bacterial genes found in certain strains of Pseudomonas putida, e.g., PpG7. Indole may be present in plant tissue or seeds and, if converted to indigo in sufficient amounts, the indigo is detectable in the plant visibly (e.g., by optical scanning device). In the case of seeds, detection may be either directly or after slitting the plant. If indole is not present in the plant, the introduction of the procaryotic gene for tryptophanase or tryptophan synthetase (subunit alpha) into the plant by transformation will permit production of indole from tryptophan or indole-3-glycerol phosphate, respectively, already present in the plant. Napthalene dioxygenase is encoded by an operon, i.e., a group of genes (in this case, four), each encoding a subunit of the enzyme. See B. Ensley et al., *Science*, 222, 167-69 (1983). Depending on the particular plant being transformed, some or all of the genes in the group can be introduced.

Another type of expressive marker is an assayable marker. An example of such a marker is a gene for an enzyme that brings about the synthesis of an opine (e.g., nopaline) by the plant. The nopaline marker (gene for nopaline synthase) is present in some Agrobacterium Ti plasmids within the T region (nos Ti plasmids). See P. Zambryski et al., *EMBO J.*, 2, 2143-50 (1983); L. Otten et al., *Biochim Biophys. Acta.*, 527, 497-500 (1978). Such a marker can be linked to a male sterile locus in accordance with the invention.

A conditional expressive marker is a marker, the presence of which is detectable or assayable in the plant (or in tissues removed from the plant) upon the application of a chemical. That is, the expression of such a marker is conditional upon application of a chemical. As used herein, the term conditional expressive marker embraces chromogenic markers, resistance markers and dominant conditional lethal markers.

A chromogenic conditional expressive marker is one which yields a detectable color upon application of a color-developing agent. The marker can be dominant or recessive, as long as it is in coupling phase with the male sterility locus (where the target locus is a male sterile locus). Such a marker, when closely linked to a male sterility locus, permits identification of male fertiles or male steriles based upon color. If it is the male sterile in which color develops, i.e., if the marker is recessive, dosages must be available such that color development is observable but not substantially deleterious to seed set, seed development or seed production.

A preferred chromogenic marker is beta-lactamase. This enzyme, encoded for by dominant bacterial genes found in a wide variety of bacteria including *E. coli*, brings about color change in a number of different substrates. See A. Bourgault et al., *J. Clinical Microbiology*, 9, 654-56 (1979). For instance, nitrocefin is converted from yellow to red, K. Shannon et al., *J. Antimicrobial Chemotherapy*, 6, 617-21 (1980); pyridene-2-azo-p-dimethylaniline cephalosporin (PADAC) is converted from a purple to yellow, R. N. Jones et al., *J. Clinical Microbiology*, 15, 677-83 (1982); and benzylpenicillin, in the presence of bromcresol purple, is converted from purple to yellow, W. L. Boyko, Anal. Biochem., 12, 85-88 (1982). A plant transformed with beta-lactamase, upon application of any of the above substrates, will be assayable based on the color change. Close linkage to male fertility/male sterility will permit a corresponding assay for male steriles.

Another chromogenic marker of choice is the gene for beta-galactosidase. This enzyme, encoded by dominant bacterial genes found in various bacteria including *E. coli*, converts o-nitrophenyl-beta-D-galactoside (ONPG) to yellow; 5-bromo-4-chloro-3-indolyl-beta-D-galactoside (XG) to blue; and 6-bromo-2-naphthyl-beta-D-galactoside, in conjunction with 4-benzoylamino-2,5-dimethoxyaniline, to blue. See J. H. Miller, *Experiments in Molecular Genetics*, Cold Spring Harbor Laboratory, New York, pp. 48-49, 54-55 (1972).

A resistance conditional expressive marker is a marker which permits assay for its presence by application of the chemical, e.g., an antibiotic or a herbicide, for which resistance is provided by the marker. The chemical to be applied to the plant is one which in the absence of resistance confers some observable damage to the plant without unduly weakening it. The marker is normally dominant for resistance and is in coupling phase with the male fertility allele to which it is linked (where the target locus is a male sterile locus). If the conditional expressive resistance marker is recessive, it can also be used in accordance with the invention by linkage in coupling phase, which will permit identification and removal of the male fertiles (sensitive). The test for resistance is administered by applying the antibiotic (e.g., kanamycin) to the plant at a dosage independently determined to cause detectable but non-systemic tissue necrosis. That is, the effect of the antibiotic on the sensitive plants (e.g., the male steriles when closely linked) is visible but non-lethal tissue discoloration or necrosis.

An antibiotic resistance marker of choice is kanamycin resistance. The gene for resistance encodes for aminoglycoside 3'-o-phosphotransferase II, an enzyme which confers resistance to certain antibiotics including kanamycin, neomycin and G418. Plants can be tested for resistance by the ability of detached shoots to root in the presence of antibiotic (e.g., kanamycin sulfate at 10 mg/l) on MS agar, or by the ability of an excised segment of a leaf to form callus on callus medium supplemented with antibiotic (e.g., kanamycin sulfate at 100 mg/l). Depending on the system, another useful way to score presence of a resistance marker would be to spray leaves of seedlings. The leaves of sensitive plants (corresponding to homozygous nuclear male steriles), upon treatment with antibiotic in appropriate dosage, develop necrotic lesions; plants with resistance (corresponding to the male fertile phenotype) would not. In tomato, for instance, application of kanamycin over a broad concentration range of approximately 75 to 200 micrograms/ml permits identification of plants containing the marker, with full recovery and normal flowering of the plants. Seedlings are sprayed and after 7-14 days the phenotype is scored. Transformation with the gene for kanamycin resistance is described in R. T. Fraley et al., Proc. Natl. Acad. Sci., 80, 4803-07 (1983), and in M. De Block et al., *EMBO J.*, 3, 1681-89 (1984).

Another example of a resistance marker is the gene for resistance to the antibiotic chloramphenicol. The gene for resistance, found in enteric bacteria including *E. coli*, encodes chloramphenicol acetyl transferase. See M. De Block et al., *EMBO J.*, 3, 1681-89 (1984); Herrera-Estrella et al., *Nature*, 303, 209-13 (1983). Other examples are the markers for methotrexate resistance and hygromycin resistance.

Another type of conditional expressive marker is a dominant conditional lethal marker. Such markers are genes encoding enzymes which can convert a precursor into a phytotoxin. Upon application of the precursor to the plant, e.g., in a chemical spray, the presence of the marker results in conversion of the precursor into a chemical lethal to the plant. For use with a male sterile target locus the conditional lethal marker gene is dominant and is linked in coupling to the dominant male fertile allele (a recessive conditional lethal would kill the male steriles). Upon application of the precursor, male fertile plants are subjected to the effects of the toxin whereas male sterile plants are unaffected. This provides a means of obtaining a row of male steriles without need for individual inspection or physical rogueing.

A broad class of genes, many of them of bacterial origin, can be employed in a conditional lethal system. In general, the genes for any enzyme or series of enzymes that function as an antibiotic synthetase can be conditional lethal markers if the precursor (i.e., the compound converted to the antibiotic by the antibiotic synthetase) is non-phytotoxic and if it is not produced by the plant. The invention embraces novel plants transformed with dominant conditional lethal markers, preferably where the marker is closely linked to a target locus.

A conditional lethal marker of choice is the iamH gene, encoding the enzyme indole acetamide hydrolase (IAMH), found in *Agrobacterium tumefaciens*. The enzyme can convert acetamides to acetic acids. The gene is available and can also be obtained from Agrobacterium. See D. Inze et al., *Mol. Gen. Genet.*, 194, 265–74 (1984). For instance, (iamH) converts indole acetamide (IAM) to indole acetic acid (IAA). It also converts naphthalene acetamide (NAM) to naphthalene acetic acid (NAA), a compound of substantially greater toxicity to plants. Tobacco and tomato are sensitive to NAA at a spray dosage above 0.5 mg/ml. If the gene for IAMH is introduced into a plant, e.g., using Agrobacterium, spraying of the plant with NAM will result in the production of NAA and consequent plant death. If the plant has the dominant iamH gene linked in coupling phase to the male fertility allele in accordance with the method of the invention, spraying a mixture of male fertiles and male steriles with NAM will result in destruction of male fertiles. Other examples of dominant conditional lethal markers are the genes for methoxinine dehydrogenase (converts methoxinine, or 2-amino-4-methoxy-butanoic acid, to methoxyvinyl glycine in *Pseudomonas aeruginosa*), R. Margraff et al., *Experientia*, 36, 486 (1980); and rhizobitoxine synthetase (produces rhizobitoxine, or 2-amino-4-(2-amino-3-hydroxy-propoxy)-trans-3-butenoic acid in *Rhizobium japonicum*), L. D. Owens et al., *Weed Science*, 21, 63–66 (1973).

Dominant conditional lethal markers introduced into plants in accordance with the invention may serve as selective plant removal agents in contexts other than hybrid breeding. When a target locus other than male sterile is tightly linked in coupling to such a marker, plants containing the target locus can be selected (or identified) based on the presence of the marker in a way analogous to that described herein for a male sterile target locus. In other contexts, dominant conditional lethal markers have uses apart from close linkage. For instance, a ground cover crop (or a ground cover which is a common weed) containing such a conditional lethal gene, introduced by transformation, can be killed by application of the appropriate precursor, thereby freeing an entire field for replanting. Another use is to remove volunteer seedlings from the previous crop in a crop rotation situation. An additional use is to weaken or remove one crop selectively in a polyculture situation.

Transformation of a plant to insert a marker can be accomplished at the whole plant level, the organ or tissue level, the cell level or the protoplast level, using any one of a number of transformation techniques known in the art which will lead to integration of the introduced gene into the nuclear genome of the plant. For instance, as described further below, *Agrobacterium tumefaciens* or *Agrobacterium rhizogenes* can be used to transform a plant. Transposons can also be used to introduce genes into plants. Alternatively, naked DNA transformation of plants, e.g., transformation of plant protoplasts, may be brought about with various techniques, for instance, the use of polycations or polyethylene glycol, the use of electroporation (electric fields), or the use of mechanical delivery by microinjection. See M. Saul et al., Programme and Abstracts NATO Advanced Studies Institute, FEBS Advanced Course, E15 (1984).

*Agrobacterium tumefaciens* and *Agrobacterium rhizogenes* are species of bacteria which in nature can infect a plant at a wound site, in the process causing tumor formation but also introducing some of the DNA of the Agrobacterium into the plant for chromosomal take-up. The introduced DNA (transferred DNA, or T-DNA) is carried on the Ti (tumor-inducing) plasmid of Agrobacterium. This system, in particular *Agrobacterium tumefaciens*, has been studied and modified for use as a vector system in plant transformation. Techniques are known for deleting that part of the Agrobacterium genome (the onc region) which causes tumor formation (i.e., disarming the plasmid) and for inserting foreign DNA into the T region of the Ti plasmid for introduction into the plant. As used herein, the term T-DNA refers to any DNA carried between and including the left border (LB) and right border (RB) sequences of the Ti plasmid. LB and RB are the only sequences required in cis for transfer of DNA from Agrobacterium to a plant cell. Other functions, e.g., virulence or vir genes, may be present in trans. In certain Agrobacterium strains carrying octopine Ti plasmids there are two T-DNA regions, known as TL-DNA and TR-DNA, each bounded by its own LB and RB sequences. In pTi15955, TL and TR are separated by shorter DNA segment called TC-DNA (R. F. Barker et al., *Plant Molecular Biology*, 2, 335–50 (1983)).

Various plasmid vectors have also been developed for use in the Ti system. See L. Ream et al., Science, 218, 854–59 (1982); M. W. Bevan et al., Ann. Rev. Genet., 16, 357–84 (1982); P. Zambryski et al., European Patent Application No. 116,718, published Aug. 29, 1984; R. Fraley et al, *Proc. Natl. Acad. Sci.*, 80, 4803–07 (1983); M. Bevan et al., *Nature*, 304, 184–87 (1983); and P. Zambryski et al., *Genetic Engineering Principles and Methods*, Vol. 6, J. Setlow et al. eds., 253–78 (1984); Also, see A. Hoekema et al, *Nature*, 303, 179–80 (1983) regarding use of a binary vector system in Agrobacterium.

Agrobacterium can be used to transform plants in various ways including inoculation of wounded plant tissue (e.g., stem inoculation or leaf disc inoculation) and protoplast cocultivation. The transformed plants may be dicotyledenous or monocotyledonous (see G. M. S. Hooykaas et al., *Nature*, 311, 763–64, (1984). Agrobacterium may be used for the method of the invention with any plant which is transformable by Agrobacterium with stable uptake into the plant genome and which, where necessary, is regenerable after such transformation.

There have been reports of the use of Agrobacterium to introduce various genes into plants. For instance, Agrobacterium has been used to introduce the chloramphenicol acetyltransferase and octopine synthase genes in tobacco, with stem inoculation, L. Herrera-Estrella et al., *Nature*, 303, 209–13 (1983); the neomycin phosphotransferase II (kanamycin resistance) gene in tobacco with stem inoculation, see M. W. Bevan et al., *Nature*, 304, 184–87 (1983) and references cited above in discussion of kanamycin resistance as a marker; and the dihydrofolate reductase gene in tobacco with cocultivation, L. Herrera-Estrella, *EMBO J.*, 2, 987–95 (1983).

Transformation of plants using Agrobacterium can be carried out using known methods of gene enhancement or control. Promoter systems known in the art can be employed to bring about or ensure adequate expression of the marker. Promoters of choice include the nopaline synthase promoter, the carboxylase small subunit promoter, the chlorophyll A/B binding protein promoter, and the promoters of the TR 1' and 2' agropine genes, J. Velten et al., *EMBO J.*, 3, 2723–30 (1984).

Regeneration of plants transformed with Agrobacterium may be by techniques of regeneration from plant protoplast, plant callus or plant tissue known in the literature. See, e.g., D. L. Bidney et al., Protoplasma, 117, 89–92 (1983) (cabbage); K. Glimelius et al., *Protoplasts* (I. Potrykus ed., Birkhauser Verlag Basel), 64–65 (1983) (rapeseed); R. P. Hangarter et al., *Plant Physiol.*, 65 761–67 (1980) (tomato) and R. Horsch et al., *Science*, 277, 1229–31 (1958) (tomato leaf disc method). Regenerated plants of normal morphology should be selected. Also, the ploidy of the regenerants is preferably the same as that of the starting material; this can be verified by microscopy.

Inducible promoters can also be employed with the invention, in particular in conjunction with the introduction of a dominant lethal marker, which combination in effect becomes a dominant conditional lethal and which combination is to be considered a dominant conditional lethal marker for present purposes. For instance, a metallothionein promoter (of yeast or plant origin) is inducible with copper; the *E. coli* lac operon promoter is inducible with lactose or isopropyl thio-beta-D-galactoside (IPTG); and the Tn10 tetracycline resistance promoter is inducible with tetracycline. If a lethal marker is under the control of an inducible promoter, it is conditionally lethal such that application of the inducing agent will cause the marker to function as a lethal agent.

Transformation of a plant in accordance with the method of the invention preferably results in the introduction of the foreign gene (the marker) as a single locus insertion in a fraction of the plants and more preferably in at least a substantial fraction of the plants. Single locus insertion can be shown by screening of progeny in crossing experiments, and single locus transformants can be selected. If the transformation involves multiple (i.e., more than single) locus introduction, single locus transformants can be obtained through conventional breeding to segregate single locus progeny. That is, the transformants can be outcrossed until monohybrid segregation ratios are obtained. In general, the Agrobacterium system transforms plants by substantially single locus insertion. See R. B. Horsch et al., Science, 223, 496–98 (1984), and M. DeBlock et al., *EMBO J.*, 3, 1681–89 (1984). Single locus transformants are heterozygous for the marker. The single or multiple nature of the insertion can also be determined using molecular techniques such as Southern blotting.

Transformation of the plant also preferably results in the introduction of the foreign gene (the marker) into the host plant genome in a substantially random fashion with respect to genetic location, thereby expediting the task of selecting a plant with close linkage. That is, the probability of a given group of transformed plant cells having the introduced gene closely linked to a particular locus, e.g., a male sterile locus, correlates with the extent of randomness of the introduction. However, absolute randomness is not necessary for the method of the invention. Rather, there need only be a sufficient number of sites to which foreign DNA can be introduced to permit the production of a plant with the introduced gene closely linked to a target locus (e.g., a male sterile locus). The extent of randomness in transformants can be shown by mapping or by DNA analysis (e.g., Southern blot). In the case of a male sterile locus, as stated, for many plants there will be a number of such loci in a given plant species. The Agrobacterium system is a preferred system for introducing DNA into a host plant in a substantially random manner. See M. DeBlock et al., *EMBO J.*, 3, 1881–89 (1984).

In accordance with the invention a group of plant transformants is obtained containing the introduced marker. Depending on the size of the group, some of the plants may have the marker linked to a male sterile gene. Of these, some may have the marker gene closely linked (coupled) to a male sterile gene. Using the method of the invention linkage as close as about 0.5 or even about 0.1 recombination unit is possible. Selection of a transformant with the desired linkage can be accomplished by making a series of crossings of the transformants, followed by progeny scoring (meaning testing or analyzing the progeny to determine segregation patterns) in known ways in order to determine the relative abundance of each phenotypic class and in order to select for a plant with the marker gene linked to the male sterile locus. Assuming that introduction of loci occurs randomly on the genetic map, the likelihood of obtaining a plant of a given closeness of linkage can be calculated in view of the number of male sterile genes involved, the size of the genome, and the number of transformants tested. The probabilities increase with the number of transformants and the number of ms loci, and decrease with departures from absolute randomness.

Linkage can also be determined using molecular techniques, e.g., allozyme markers or restriction fragment length polymorphism markers, to identify close-linkage transformants. See S. D. Tanksley, Plant Molec. Bio. Rptr., 1, 3–8 (1983) and references cited therein. Mapping a transformant with respect to an introduced marker and a known allozyme marker will reveal any linkage between the two. If there is linkage to an allozyme marker, and if the allozyme marker also has a known natural linkage to a male sterile locus, the linkage (if any) between the introduced locus and the male sterile locus can be determined. For instance, in tomato it is known that the allozyme locus Prx-2 is within 1 unit of ms10 and the allozyme locus Skdh-1 is within 1 unit of ms32; C. M. Rick et al., *Isozymes: Current Topics in Biological and Medical Research*, Vol. II, 269–84 (1983). Thus, if the distance between an introduced marker and the allozyme locus Skdh-1 is determined for a transformant, that distance, plus or minus 1 unit, is the distance between the introduced marker and ms32.

Selection of close linkage involves selection for linkage of marker genes and male sterile genes in coupling phase. That is, the dominant alleles of the male sterile locus and the marker locus are on the same chromosome, resulting in cosegregation upon crossing. If close linkage is found which is not in coupling, i.e., linkage in repulsion, linkage in coupling can be obtained by conducting crossings to select a recombinant, in ways known to those skilled in plant breeding.

Another type of linkage embraced by this invention is the use of flanking markers, that is, the use of two different markers on either side of the nuclear male sterile gene. This approach results in closeness of linkage which is superior (closer) than either of the individual markers alone would provide for a given linkage distance. Thus, linkage of 10 units with each of two different flanking markers is approximately equivalent to linkage of less than one unit with a single marker. This approach is particularly useful if tight linkage is not readily obtained (e.g., due to departures from randomness) using non-flanking markers.

A transformed plant with introduced marker gene closely linked to a target locus, once selected, can be used in breeding programs any time there is a need or desire to follow the presence or absence of the target locus in a plant from generation to generation. In the case of male steriles, this method permits the identification of male sterile plants directly, without need for crossings to determine whether the plant is fertile or sterile. The method can also be useful in genetic studies and breeding programs for marking or tagging other genes, particularly those difficult to score (e.g., disease resistance).

In the case of a male sterile locus as target locus, the method of the invention embraces use of a plant as starting material which already has a male sterile gene present either in homozygous or heterozygous form, e.g., a commercially available male sterile mutant line. The method also embraces the introduction of a male sterile gene into a male fertile plant (either homozygous or heterozygous for male fertility) prior to or subsequent to transformation with a marker. Where the male sterile gene is introduced, the introduction may be accomplished using standard crossing techniques known to plant breeders. For instance, crossing a plant (transformant or otherwise) which is homozygous for male fertility (Ms/Ms) with a plant which is homozygous for male sterility (m/ms) yields heterozygous plants (Ms/ms). A subsequent backcrossing of the heterozygous plants with the plant homozygous for male sterility (ms/ms) yields a 50:50 mixture of heterozygous (Ms/ms) and homozygous (ms/ms) plants. Crossing a plant (transformant or otherwise) which is heterozygous for male fertility (Ms/ms) with a plant which is homozygous for male sterility yields a 50:50 mix of heterozygous (Ms/ms) and homozygous (m-/m) plants.

Selection of a close-linkage transformant is made by appropriate crossings and progeny scoring. A general procedure for this is described below, with male sterile locus as target locus, with the understanding that, as understood by those skilled in plant breeding, variations in the steps or in the sequence of the steps can lead to comparable results. The general procedure calls for transformation of homozygous male fertile plants (Ms/Ms) as a first step. It should be understood that analogous procedures may be followed where the first step is transformation of a plant heterozygous for male fertility (Ms/ms) or homozygous for male sterility (ms/ms). The procedure described below uses as a marker the (dominant) conditional expressive antibiotic resistance marker kanamycin resistance (KanR), but the procedure would be analogous for other markers.

A plant homozygous for male fertility (Ms/Ms) is transformed to yield a group of transformants which, assuming single locus transformation, are heterozygous for the introduced marker. If the marker is KanR, the plant is heterozygous for kanamycin resistance (KanR/—), or more strictly, hemizygous for KanR (when KanR is introduced by transformation into a given chromosome, the homologous chromosome has only a deficiency, i.e., the (—) allele has no physical existence and is defined operationally). Subsequently each transformant is tested to determine if the introduced gene (KanR) is present as a single locus. Each transformant is either self-crossed or crossed with a kanamycin sensitive (—/—) plant to make this determination. Segregation of 3:1 (that is, 3 kanamycin resistant to 1 kanamycin sensitive) in self progeny or 1:1 in cross progeny is consistent with single locus segregation. For instance, as shown in FIG. 1 ("I. Dingle locus determination"), single locus introduction of the marker into the transformant (KanR/—) is shown if, in a cross of the transformant with a line which is homozygous kanamycin sensitive plant (—/—), the progeny segregate 1:1 (resistant:sensitive). The larger the number of progeny scored, the greater is the meaningfulness of the segregation data (the maximum being limited only by the number of seeds set and the number of crosses performed). At least forty progeny per transformant are recommended. Transformants with multiple introduced loci are discarded, or backcrossed until single locus segregation is obtained.

Each transformant shown to be single locus is tested for close linkage. Each transformant (Ms/Ms) is backcrossed to a homozygous male sterile (ms/ms) line to yield first-generation progeny heterozygous for both marker and male fertility (this step is unnecessary if the transformant is already heterozygous for male fertility). The crossing step is preferably repeated for each of a number of different male sterile lines, each line being homozygous for a different ms gene. The more lines that are used, the less important is any departure from randomness of marker insertion with respect to the genetic map. The first-generation progeny are backcrossed to the respective homozygous male sterile lines to yield second-generation progeny which segregate for both ms and marker loci, and which are scored for linkage. Linkage in the parent transformant is determined by the degree of association between marker and ms loci in the second-generation progeny. Absolute (or near absolute) linkage in coupling is demonstrated for a given transformant where the second-generation progeny are all fertile resistant or sterile sensitive (absolute linkage in repulsion is shown if the progeny are all fertile sensitive or sterile resistant). For instance, as shown in FIG. 1 ("II. Linkage determination"), absolute linkage is shown if, in a cross of a transformant heterozygous for male fertility and kanamycin resistance (Ms/ms;KanR/—) with a line homozygous for male sterility and kanamycin sensitivity, progeny segregate only fertile resistant and sterile sensitive plants, with no recombinant plants (fertile sensitive or sterile resistant); non-linkage is shown by equal proportions of fertile resistant, fertile sensitive, sterile resistant, and sterile sensitive. The fewer fertile sensitive and sterile resistant plants (i.e., recombinant plants) relative to fertile resistant and sterile sensitive plants, the closer is the linkage. Again, the larger the number of progeny scored, the greater the reliability of the linkage data. Where sufficiently close linkage is shown, the heterozygous male parent which is the parent of the close-linkage second-generation progeny is selected for use in hybrid breeding (or for crossing into other breeding lines or varieties of the species). If desired, verification of the close linkage may be made by additional crossings.

If the above procedure is followed for a plant with a typical total genomic length of approximately 1000 recombination units (e.g., tomato, barley, corn) and for which, e.g., five independent male sterile loci are used (i.e., five different lines, each with a different male sterile locus), it is necessary to screen approximately 299 transformants carrying a single marker locus in order to attain an approximate 95% probability of finding a plant having an introduced marker locus within one map unit of a male sterile locus, assuming random integration. To achieve a 95% probability for other levels of closeness, it is necessary to screen approximately 99 plants for a closeness of 3 units; 59 plants for a closeness of 5 units; 29 plants for a closeness of 10 units; 14 plants for a closeness of 20 units; and 11 plants for a closeness of 25 units. Each of the transformants (e.g., each of the 299) is subjected to backcrossing and progeny scoring as described above in order to select for the desired closeness of linkage. Once the close-linkage plant is obtained, the male fertile phenotype can be predicted by the presence of the marker, with an accuracy proportional to the degree of linkage.

A general procedure is described below for use in hybrid breeding of a close-linkage plant made in accordance with this invention, again with the understanding that variations in the steps or in the sequence of the steps, as understood by those skilled in plant breeding, can lead to comparable results. The procedure is described using the (dominant) conditional expressive antibiotic resistance marker KanR, again with the understanding that the procedure is analogous for other markers.

A homozygous male sterile plant (ms/ms) is crossed with an inbred line (Ms/Ms) destined to be the female parent in hybrid production. The cross yields first-generation (F1) progeny heterozygous for male fertility (Ms/ms). The F1 progeny are backcrossed to the inbred and from the first-generation backcross progeny (BC1) heterozygous male fertile (Ms/ms) plants are selected by progeny testing. The selected BC1 progeny are backcrossed several times to the inbred line to maximize selective introduction of the male sterile gene into the inbred's genome. Lastly, heterozygous (Ms/ms) progeny are self-crossed to produce a homozygous (ms/ms) inbred line.

In parallel, an analogous procedure is carried out for a close-linkage plant, homozygous for male fertility (Ms/Ms) and marker (KanR/KanR). (The close-linkage plant as originally selected can be converted to this homozygous form by appropriate crossings and selections, as explained previously.) The close-linkage plant is crossed with the same inbred line as above (ultimate female parent), the F1 progeny are backcrossed to the inbred, and plants heterozygous for marker (KanR/—) are selected. The selected BC1 progeny are backcrossed several times to the inbred line to maximize selective introduction of the closely linked marker gene into the inbred's genome. Heterozygous (KanR/—) progeny are selfed to produce a homozygous (KanR/KanR) inbred.

The two inbreds resulting from the above, one carrying the male sterility allele and the other carrying the marker closely linked to the male fertility allele, but otherwise nearly isogenic, are crossed to generate progeny from which a maintainer line is selected. The close-linkage maintainer line is heterozygous for male fertility (Ms/ms) and for closely linked marker (KanR/—).

The maintainer line is backcrossed to a homozygous male sterile and kanamycin sensitive line (ms/ms;—/—), e.g., the female parent of the maintainer line, to yield a mixture of, first, plants homozygous for both male sterility (ms/ms) and absence of marker (—/—) and, second, plants heterozygous for male fertility (Ms/ms) and closely linked marker (KanR/—). The mixture of plants is planted as the female parent for hybrid breeding, e.g., as the female row in a hybrid crossing row. Testing of all the plants in this row for presence of the marker, which in effect is a test for male fertility, permits removal of male fertile plants at an early stage.

Identification and removal of the male fertiles from the aggregation of male fertiles and male steriles resulting from crossing of the maintainer line is accomplished in different ways depending on the marker which is closely linked. In each case, however, removal occurs at a pre-anthesis stage, preferably at the seed or seedling stage. If the marker is a visible expressive marker, the presence or absence of color (depending on whether the marker is dominant or recessive) is the basis for identifying and removing male fertiles. If the marker is a non-visible but assayable expressive marker, an appropriate assay is conducted, e.g., on a piece of leaf. If the marker is a conditional marker, e.g., chromogenic, resistance, or dominant conditional lethal, the chemical agent in question may be applied, e.g., in a spray directed to either part of the plant or all of the plant, at a dosage independently determined to be effective given the level of expression of the marker in the close-linkage plant. In the case of a chromogenic marker the presence or absence of developed color (depending on whether the marker is dominant or recessive) is the basis of identification. In the case of resistance markers, which are normally dominant, absence of observable damage to the plant tissue to which the chemical is applied is the basis of identification of male fertiles. For KanR, the test may be carried out by growth of an excised plant part, e.g., leaf or stem, in the presence of the antibiotic in appropriate dosage in sterile culture. Tissue from male fertiles will grow; tissue from male steriles will not. Once identified as male fertiles based upon chromogenic or resistance markers, male fertiles are removed, e.g., by hand or mechanically in the field or, e.g., by optical scanner and sorter if identification is by color at the seed level. In the case of dominant conditional lethal markers, application of the chemical, which may be best accomplished by spraying the entire plant or field, automatically and selectively weakens or destroys the male fertiles, preferably without need for physical removal.

Removal of male fertile plants results in an essentially pure set of male sterile plants. The essentially pure set of male sterile plants is used as the female parent stand in hybrid crossing. This stand is interplanted with stands of the intended male parent and hybrid seed results from pollination by wind or insects. Alternatively, pollination can be by hand. Selectively harvesting the female parent rows yields essentially pure hybrid seed. The maintainer line, which is heterozygous for both male fertility and marker, may be maintained indefinitely by appropriate crossings and selections, as described above and as understood by those skilled in plant breeding.

EXAMPLES

In the following examples, reagent materials are commercially available, unless otherwise specified. Enzymes used in the cloning procedures are available from commercial sources. Restriction endonuclease reactions are carried out according to manufacturer instructions. Unless otherwise specified, the reaction conditions for other reactions are standard conditions used in the art, as described, for example, in T. Maniatis et al., *Molecular Cloning*, Cold Spring Harbor Laboratory, New York (1982) (referred to herein as "Maniatis"); R. W. Davis et al., *Advanced Bacterial Genetics*, Cold Spring Harbor Laboratory, New York (1980); D. A. Evans et al., *Handbook of Plant Cell Culture*, Vol. 1, ed., MacMillan, New York (1983); and J. H. Miller, *Experiments in Molecular Genetics*, Cold Springs Harbor Laboratory, New York (1972) (referred to herein as "Miller").

Plasmids pBR322 and pUC8 are multicopy plasmid vectors, available commercially, Bolivar et al., *Gene*, 2, 95-113 (1977); J. Veira et al., *Gene*, 19, 259-268 (1982) (referred to herein as "Veira"). Plasmid DNA was prepared by alkaline extraction according to H. C. Birnboim et al., *Nucleic Acids Res.* 7, 1513-1523 (1979) (referred to herein as "Birnboim"), unless stated otherwise. All ligation reactions were performed in a final volume of 20 microliters (ul). at 15° C. for 16 hours with 400 units T4 DNA ligase. Transformations of *E. coli* strains were performed according to M. Dagert et al., *Gene*, 6, 23-28 (1979) (referred to herein as "Dagert").

M9, minA, and LB media are described by J. H. Miller, *Experiments in Molecular Genetics*, Cold Spring Harbor Laboratory, New York (1972). MS medium is described by Murashige et al., *Physiol. Plant*, 15, 473-97 (1962) (referred to herein as "Murashige"). Micrograms are referred to herein as ug; microliters are referred to herein as ul; and nanograms are referred to as ng.

EXAMPLE 1

Introduction of Resistance Conditional Expressive Marker (KanR) into Tomato Hybrid

A. Preparation of *Agrobacterium tumefaciens* C58Cl/pGV3850 kanR

*Agrobacterium tumefaciens* C58Cl/pGV3850 kanR contains acceptor Ti plasmid pGV3850 kanR which can (1) transfer T-DNA to plant cells; (2) "accept" intermediate vectors having homology to pBR322 sequences carried on pGV3850 kanR; and, (3) direct nopaline synthesis and confer kanamycin resistance upon transfer of T-DNA to plant cells. See P. Zambryski et al., European Patent Application No. 116,718 (published Aug. 29, 1984) for a general description of such plasmids and this approach.

Plasmid pGV3850kanR was constructed using pGV3850 (P. Zambryski et al., *EMBO J.*, 2, 2143-50 (1983)) and pLGV232neo (generally available). Plasmid pLGV232neo is a derivative of pLGV23neo (Herrera-Estrella et al., *EMBO J.*, 2, 987-95 (1983)) constructed by introduction of the ocs (octopine synthase) 3' tail fragment to the Tn5 SmaI site in pLGV23neo. Plasmid pLGV232neo can be reconstructed from (1) plasmid pLGV23neo and (2) plasmid pSS155 (S. Schweitzer et al., *Plasmid*, 4, 196-204 (1980)), containing a PvuII fragment with an ocs polyA signal, by ligating the fragment to the SmaI site of pLGV23neo.

The preparation of pGV3850kanR was carried out as follows. A BglII linker was introduced into the PstI site of pBR322 to yield a pBR322 derivative by digestion of pBR322 with PstI, treatment with T4 DNA polymerase (Maniatis, supra), and ligation to BglII linker (commercially available). A BglII digest of the pBR322 derivative was prepared. pGV232neo was partially digested with BclI and then digested with BamHI to yield a pGV232neo digest. The digest of the pBR322 derivative was ligated to the digest of pGV232neo. Transformation of *E. coli* strain JM83 (Veira, supra) was carried out using standard procedures (Maniatis, supra; Dagert, supra). Transformants were selected on plates containing LB medium supplemented with tetracycline (15 ug/ml) and kanamycin (50 ug/ml). A plasmid clone was obtained, with restriction sites in the sequence BglII/-Bam—BclI BclI/BglII—HindIII—Bam, by screening transformants based on restriction patterns (Birnboim, supra). The plasmid clone was digested with HindIII and Bam. The plasmid clone digest was ligated into pRK404 digested with HindIII and Bam. Plasmid pRK404, a derivative of pRK290 (G. Ditta et al., *PNAS*, 77, 7347-51 (1980)), is generally available. The resulting plasmid, pJJ108, was mobilized into strain C58Cl/GV3850 using pRK2013 (G. Ditta et al., *PNAS*, 77 7347-51 (1980)) as a helper. Exconjugants resulted from either single or double crossover events, based on pBR322 sequences present in pGV3850 and in the plasmid mobilized into GV3850. Double crossover events were selected by mating conjugants with BH101/pPHIJI (P. R. Hirsch et al., *Plasmid*, 12, 139-41 (1984)) and selecting gentamycin resistance and kanamycin resistance (pPHIJI is incompatible with pRK404 and, by selecting for pPHIJI with gentamycin, pRK404 single recombinants are driven out and only double recombinants survive). The resultant strain, *Agrobacterium tumefaciens* C58Cl/pGV3850kanR was used to introduce the KanR marker into plants.

B. Preparation of Plants

*L. esculentum* × *L. pennellii* seeds (generally available) were surface-sterilized by treatment with 70% ethanol/water for 1-2 minutes, followed by 10% commercial bleach for 30 minutes and rinsed with sterile water three times for ten minutes. These were germinated in sterile plastic containers on hormone-free MS medium under sterile conditions in a culture room or incubator (16 hour day, 5000 lux white fluorescent light, 27° C.). Seedlings were decapitated by transversely cutting the epicotyl, and tops rooted in fresh medium (plants can be maintained in culture for long periods of time by periodically passaging the tops in this manner). Standard aseptic techniques were used for all steps in shoot and tissue culture.

C. Transformation by Stem Inoculation

The following procedure was carried out generally in accordance with P. Zambryski et al., European Patent Application No. 116,718 (published Aug. 29, 1984).

Epicotyls from seedlings or rooted shoots were cut transversely into segments about 1 cm long, which were held upright in normal or inverted orientation by inserting into hormone-free MS solid medium. The upper cut surface was inoculated with a fresh Agrobacterium C58Cl/pGV3850kanR culture which had been prepared as described above and grown on M9+0.4% sucrose plates (Miller, supra), supplemented with kanamycin sulfate (100 mg/l). Inoculation was done with a sterile platinum loop or toothpick with an amount of cells sufficient to cover the cut surface. These were incubated three days in an incubator (same as above except 500 lux), then the inoculated surface was excised with a scalpel as a 1-3 mm thick slice. This slice was placed upright on selective callus medium (MS medium supplemented with 2% sucrose, B5 vitamins [nicotinic acid (100 mg/l), thiamine (1 g/l), pyridoxine (100 mg/l), and myo-inositol (10 g/l); Gamborg et al., *Exp. Cell Res.*, 50, 151-58 (1968)], zeatin (0.5 mg/l), 1-naphthaleneacetic acid (1 mg/l), carbenicillin 250 mg/l, and kanamycin sulfate (50 mg/l). Four to six weeks after inoculation, kanamycin resistant calli appeared on the inoculated surfaces of slices.

D. Regeneration

Resistant calli were removed with a scalpel and transferred to fresh medium for several weeks until large enough (4-10 mm diameter) for transfer to shooting (regeneration) medium (MS supplemented with 2% sucrose or glucose, B5 vitamins (as above), and zeatin (2 mg/l)) under 5000 lux. Callus was transferred to fresh shooting medium at three week intervals until shoots formed (0-3 transfers). Shoots were rooted under 5000 lux in the following rooting medium: $NH_4NO_3$ (400 mg/l), $KNO_3$ (1010 mg/l), $MgSO_4.7H_2O$ (370 mg/l), and $CaCl_2.H_2O$ (440 mg/l) in 0.8% agar supplemented with B5 vitamins (as above), 3% sucrose, and indole-3-butyric acid (0.15 mg/l). After rooting (2-8 weeks) plants were removed from agar, planted in soil, and placed under mist in a greenhouse. 33 regenerated plants (transformants) were obtained.

E. Characterization of Transformants

1) Ploidy

Basal shoots were excised from regenerated plants and rooted with Rootone in soil. To determine ploidy, each of the regenerants was crossed to diploid *L. esculentum* (crosses between polyploid tomatoes and diploid tomatoes do not produce viable seed, i.e., only diploid transformants produce seeds when crossed to a diploid). Of 33 transformants, 12 were diploid and 21 were polyploid.

2) Kanamycin Resistance

Eleven of the twelve diploids were kanamycin resistant as judged by the ability of their shoots to root in the presence of kanamycin sulfate (10 mg/l) on MS agar and by the ability of leaf segments to form callus on callus medium supplemented with kanamycin sulfate (100 mg/l).

3) Nopaline Synthesis

Eight of the KanR plants produced nopaline as assayed by paper electrophoresis of extracts (L. A. Otten et al., *Biochim. Biophys. Acta*, 527, 497-500 (1978)).

4) Southern Blot Analysis

Southern blot analysis (Maniatis, supra) of the eleven diploid KanR transformants was used to determine the number of copies of the right border (RB) region of the T-DNA inserted into the genome of each transformant. Right border fragments were detected in the Southern blot by hybridization to homologous P32 labelled T-DNA fragments (ClaI+PvuII fragment isolated from pT37H23 (A. Depicker et al., *J. Molec. and Applied Genet.*, 1, 561-73 (1982)). Six of the eleven transformants possessed a single right border fragment; five possessed two or more right border fragments. The number of right border fragments is indicative of the maximum number of introduced genetic loci determining kanamycin resistance in the transformant. Thus, at least six of the eleven transformants tested were single locus KanR transformants.

Each of the eleven transformants was also analyzed by Southern blot in order to compare the sizes of different right border fragments. It was found that each right border fragment was distinct in size, leading to the conclusion that each was the result of a distinct insertion event. This is evidence that each introduced KanR gene was present at a different site in the plant genome, a finding consistent with the expectation that the T-DNA integrated substantially randomly in the genome.

EXAMPLE 2

Selection of Close-Linkage Plants

Seven diploid KanR transformants from Example 1 were selected for linkage analysis using allozyme markers of known chromosomal position in the tomato genome. The group of seven transformants included the six transformants determined by Southern analysis to be single copy transformants. The seven transformants were subjected to outcrossings with a commercial line of *L. esculentum* and progeny scoring to determine possible linkage relationships between the introduced KanR markers and a number of known allozyme markers.

Each transformant was found to show linkage between introduced KanR and an allozyme locus known to be positioned on a particular chromosome. Introduced loci showed genetic linkage to allozyme markers on chromosomes 1, 2, 8, 10 and 12. Male sterile loci are known to exist on four of these five chromosomes: chromosome 1 (ms6, ms32); chromosome 2 (ms2, ms5, ms10, ms15); chromosome 8 (ms8, ms17); and chromosome 10 (ms31). See C. M. Rick, *Report of the Tomato Genetics Cooperative*, 20, 2-17 (1980) with respect to ms loci in tomato. A transformant which showed genetic linkage between KanR and allozyme markers on chromosome 2 (transformant A181, one of the single locus transformants) evidenced linkage between KanR and ms loci on chromosome 2, as explained below.

The allozyme loci Est-7 (esterase-7) and Prx-2 (peroxidase-2) are known to be positioned on chromosome 2. The linkage relationships between these allozyme loci and the ms loci on chromosome 2 are known to be as follows: ms10 is 1 map unit (centimorgan) from Prx-2, with the direction (i.e., which "side" of Prx-2) being unknown; m15 is 10-12 map units from Prx-2; ms2 is 17-19 map units from Prx-2 and on the same "side" of Prx-2 compared to ms15; and ms5 is 13 units from ms2, direction unknown. The locus Est-7 is 12 units from Prx-2, on the opposite "side" of Prx-2 compared to ms15, ms2 and ms5. See C. M. Rick et al., *Isozymes: Current Topics in Biological and Medical Research*, 11, 264-84 (1983); and C. M. Rick, *Report of the Tomato Genetics Cooperative*, 20, 2-17 (1980).

Allozyme mapping of 71 progeny of A181 showed the KanR introduction to be positioned 25 map units from Prx-2 and 32 map units from Est-7. That is, the introduced KanR locus was on the same "side" of Prx-2 as ms15, ms2 and ms5. Based on the known linkage distances between Prx-2 and ms loci set forth above, the linkage measurements for the introduced KanR locus evidenced linkage of KanR to m10 (linkage distance 24-26 units), ms15 (linkage distance 13-15 units) and ms2 (linkage distance 6-8 units). (Linkage of KanR to ms5 was either 5-7 units or 19-21 units, depending on which "side" of ms2 the ms5 locus maps.)

This transformant, with KanR linked to a male sterile locus, can be subjected to appropriate crossings with a line homozygous for the desired closely linked male sterile locus, as previously described, for use in hybrid breeding.

EXAMPLE 3

Introduction of Dominant Conditional Lethal Marker (iamH) into Tobacco

A. Preparation of Agrobacterium

Figure 2:
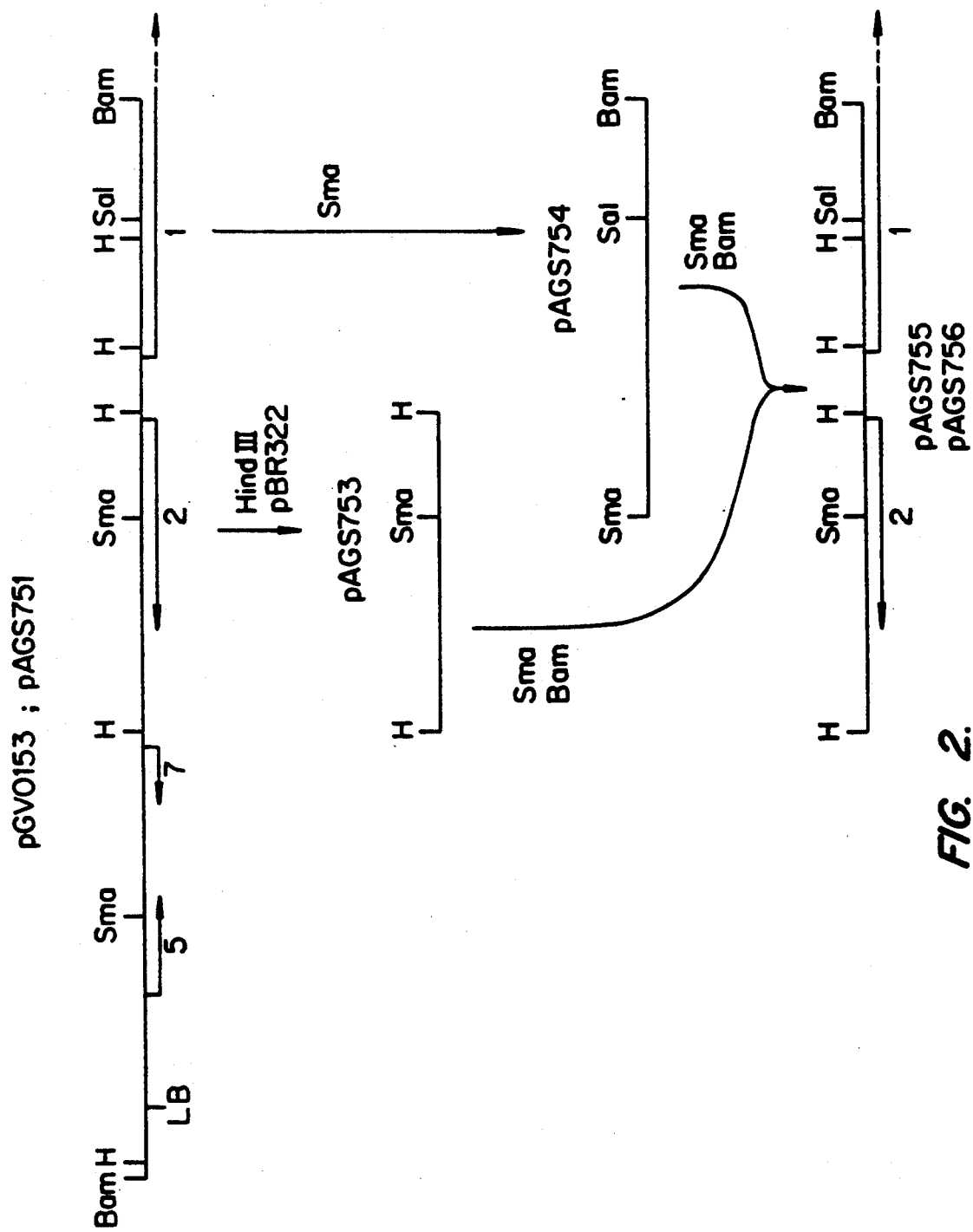
FIG. 2 is a schematic providing restriction information for plasmids pAGS751, pAGS753, pAGS754, pAGS755 and pAGS756.
Figure 3:
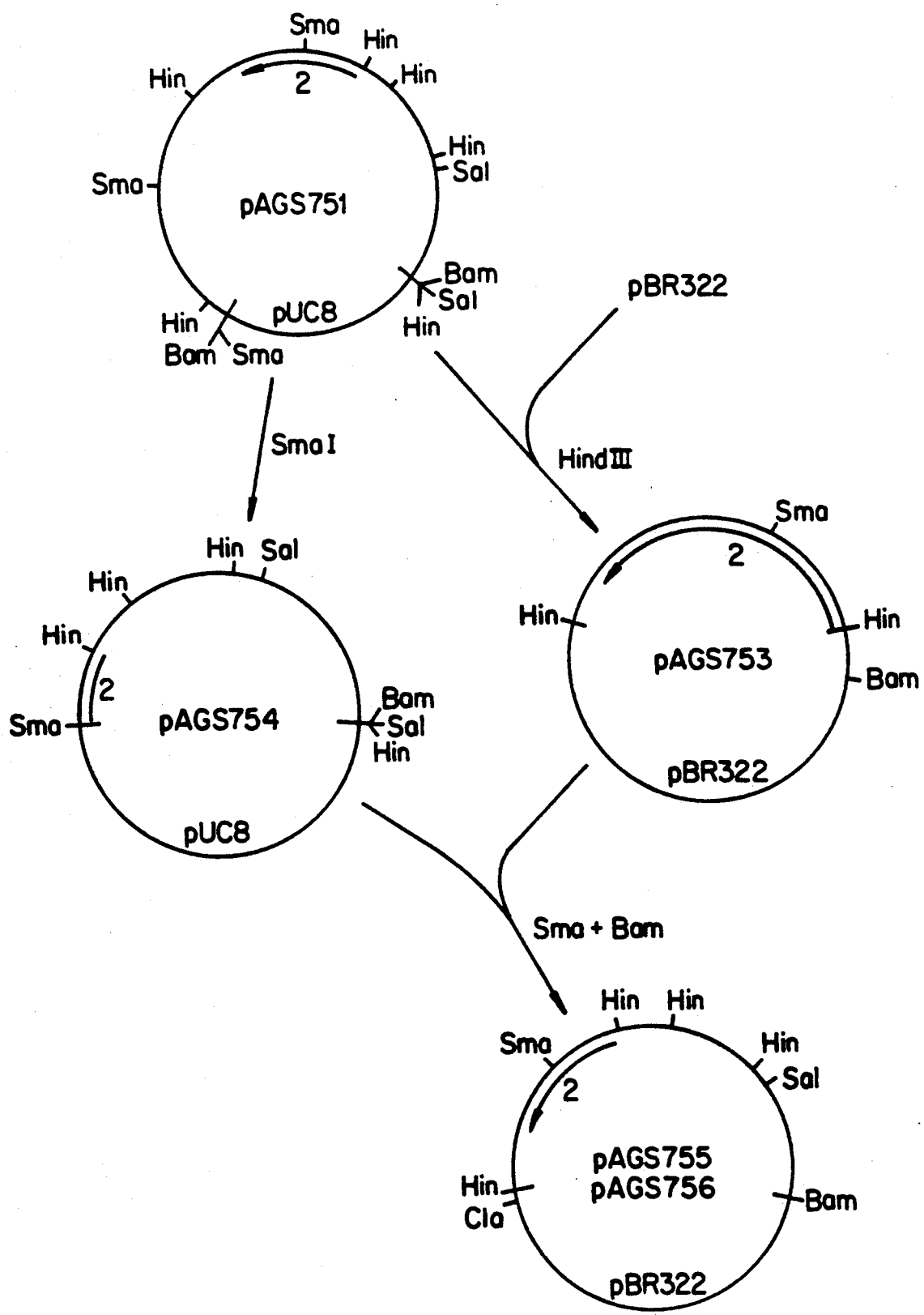
FIG. 3 is a schematic showing the preparation and restriction patterns of plasmids pAGS755 and pAGS756.
Figure 4:
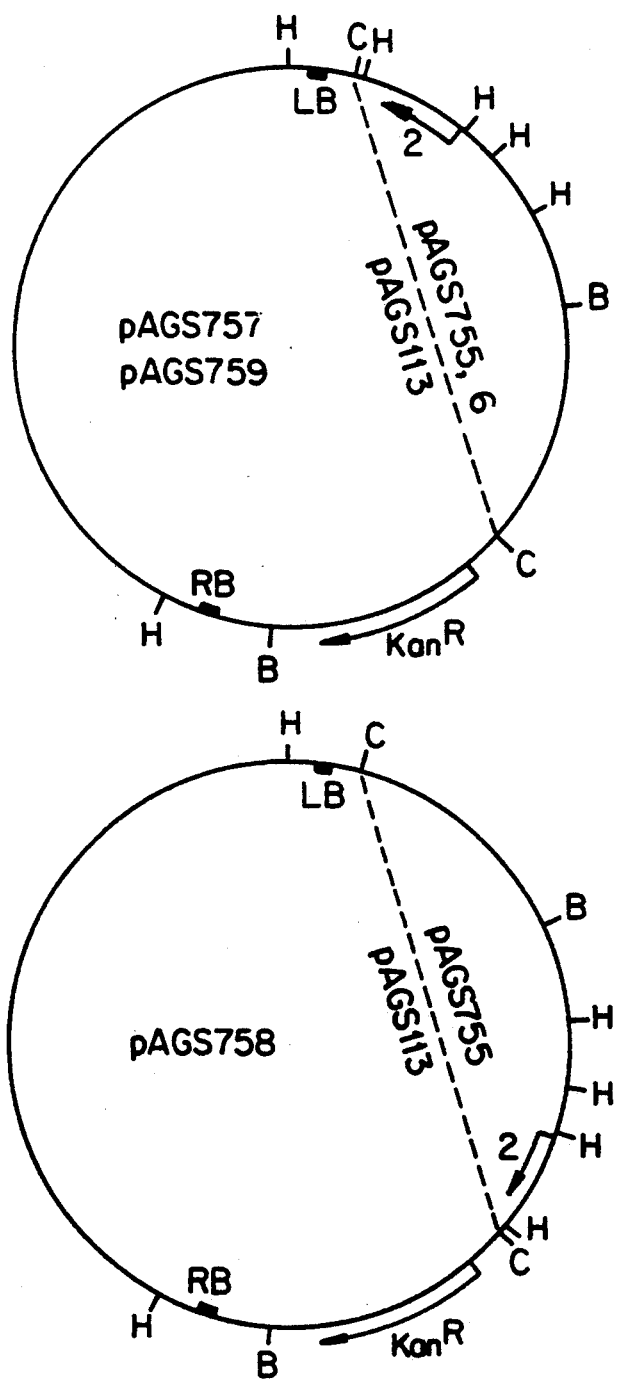
FIG. 4 is a schematic showing restriction information for plasmids pAGS757, pAGS758 and pAGS759.

The gene (iamH) for the enzyme indole acetamide hydrolase was obtained from pGV0153 (De Vos et al., *Plasmid*, 6, 249-53 (1981)) as follows (see FIGS. 2-4). Two ug of pGV0153 DNA were digested with 2 units BamHI and electrophoresed in 1% agarose. Agarose containing the Bam 8 fragment was cut out of the gel and the DNA recovered by electroelution (Maniatis, supra). The Bam 8 fragment (corresponding to the left part of TL-DNA of the octopine plasmid pTiB6S3) contained the iamH gene.

Five ug pUC8 DNA was totally digested with 5 units BamHI. 0.2 ug BamHI-cleaved pUC8 DNA was ligated to the recovered Bam 8 fragment. *E. coli* JM83 (Veira, supra) was transformed with this mixture and cells were plated on LB medium supplemented with ampicillin (100 m /l) and bromo-chloro-indolyl-B-D-galactoside (40 mg/l). Two white colonies were screened by alkaline plasmid extraction and BamHI digestion of the isolated DNA. One clone contained a plasmid with Bam 8 inserted at the BamHI site of pUC8 and was designated pAGS751. Orientation of the Bam 8 fragment in pAGS751 relative to pUC8 was determined by SalI and SmaI digestions. Plasmid pAGS751 is diagrammed in FIGS. 2 and 3. In FIG. 2, "H" refers to HindIII; "Bam" refers to BamHI; "Sma" refers to SmaI; and "Sal" refers to SalI sites. The numbers 1, 2, 5 and 7 refer to TL genes, with "2" being the iamH gene. The symbols in FIG. 3 are the same as in FIG. 2, except "Hin" refers to HindIII.

2 ul pAGS751 DNA (from alkaline extraction) was digested with BamHI and HindIII. 2 ug pBR322 DNA was totally digested with HindIII and treated with 25 units calf alkaline phosphatase. 0.2 ug CAP-treated pBR322 DNA was phenol extracted and ligated to pAGS751 BamHI and HindIII cleaved DNA in 20 ul. *E. coli* MM294 (M. Meselson et al., *Nature*, 217, 1110 (1968)) was transformed with this mixture. Cells were plated on LB medium supplemented with ampicillin (100 mg/l). Plasmid DNA extractions of twenty-four colonies were digested with HindIII and electrophoresed to identify those in which the 2.3 kb HindIII fragment was present. Two colonies (designated pAGS752 and pAGS753) carried this fragment and the vector pBR322, and were cleaved with EcoRI and SmaI to determine the orientation of HindIII 2.3 relative to the vector. pAGS753 carried fragments of 5.1 kb, 1.1 kb, and 0.5 kb, indicating the orientation shown in FIG. 3.

2 ul pAGS751 DNA (from alkaline extraction) was totally digested with SmaI. The resulting digestion was ligated and used to transform MM294. Cells were plated on LB medium supplemented with ampicillin (100 mg/l). Alkaline extraction was used to isolate DNA from 36 colonies and one (designated pAGS754) was identified by digestion with SmaI and BamHI as a deletion removing SmaI fragments 2.6 kb and 1.8 kb in size. Plasmid pAGS754 is diagrammed in FIG. 2 and 3.

pAGS753 carried the complete coding sequences of iamH and 3' sequences which carry the presumed polyadenylation sequences, but not sufficient sequence 5' to the coding sequence to provide a promoter for its transcription. pAGS754 carried complete 5' sequences but not the 3' half of the coding sequences. In order to reconstruct a functional iamH gene from these plasmids, 8 ul DNA (alkaline extraction) of pAGS753 and 2 ul DNA of pAGS754 were digested with SmaI and BamHI, and these were ligated and used to transform MM294. Cells were plated on LB medium supplemented with ampicillin (100 mg/l). Plasmid DNA was isolated from forty-eight colonies by alkaline extraction and intact plasmids were screened by electrophoresis for plasmids larger than pAGS753. Six were found and these were screened by electrophoresis of EcoRI digestions. Two were found which carried the 1.1 kb EcoRI fragment of the iamH gene. These were analyzed further by electrophoresis of digestions with BglII and HindIII. Comparison with similar digests of pAGS751 was used to demonstrate that these two plasmids (designated pAGS755 and pAGS756) contained fragments of an intact iamH gene (diagrammed in FIGS. 2 and 3).

pAGS755 and pAGS756 were each separately ligated to a binary vector designated pAGS113. See Hoekema, et al., *Nature*, 303, 179-80 (1983) regarding binary vector systems and plasmids of this type. pAGS113 is a derivative of pRK404 that carries the right and left borders of TL and the nos-nptII-ocs chimeric gene of pLGVneo2103 (generally available). Two unique restriction sites, BamHI and ClaI, lie between the TL borders of pAGS113. Plasmid pAGS113 is shown as a segment of pAGS757, pAGS758 and pAGS759 in FIG. 4. The plasmid is derivable from pAGS757 (on deposit with the ATCC as ATCC No. 53066, see below) by cutting with ClaI and ligating to circularize, as will be understood by those skilled in this area. In FIG. 4, "C" refers to ClaI; "H" refers to HindIII; "LB" and "RB" refer to left and right borders, respectively; and "2" refers to the iamH gene.

The transfer of pAGS755 to pAGS113 was accomplished as follows. 5 ng of pAGS755 and 250 ng of pAGS113 were digested with ClaI and ligated. The ligation was used to transform MM294 and cells were plated on LB supplemented with tetracycline (20 mg/l). The transfer of pAGS756 to pAGS113 and subsequent transformation and plating were carried out in the same way. Six colonies from the pAGS755 ligation and three from the pAGS756 ligation were screened by HindIII digestion of alkaline extraction plasmid DNA and compared to pAGS755 and pAGS756. One derivative of pAGS756 (designated pAGS759) was a fusion of pAGS113 and pAGS756, and two derivatives of pAGS755 (designated pAGS757 and pAGS758) were fusions of pAGS113 and pAGS755. The orientations of pAGS757 and pAGS759 were the same; that of pAGS758 was the opposite.

Transfer to Agrobacterium was accomplished as follows. Recipient *Agrobacterium tumefaciens* strain LBA4404 (Hoekem et al., *Nature*, 303, 179-80 (1983)) was grown 40 hours in min A medium at 28° C. An *E. coli* strain carrying helper plasmid pRK2013 and *E. coli* donor strains MM294/pAGS757, MM294/pAGS758 and MM294/pAGS759 were grown overnight in LB at 37° C. In three separate mixings, one ml of recipient and one ml of helper culture were mixed with one ml of one of the three donors. Three mixtures, one for each donor, were centrifuged. Pellets were taken up in 100 ul 10 mM MgSO$_4$, and the resulting suspensions spotted on LB plates which were then incubated at 28° C. overnight to allow mating to occur. Cells were washed off each plate into 2 ml MgSO$_4$. 0.1 ml of these suspensions were plated on LB plates supplemented with rifampicin (100 mg/l) and tetracycline (2.5 mg/l) and incubated at 28° C. for forty hours. Colonies were streaked out on M9 plates supplemented with sucrose (0.4%) and tetracycline (2.5 mg/l). The resultant *A. tumefaciens* cells, one isolate from each of the matings, were designated *A. tumefaciens* LBA4404/pAGS757, LBA4404/pAGS758 and LBA4404/pAGS759, respectively. (LBA4404-/pAGS757 has been deposited as ATCC No. 53066). *A. tumefaciens* LBA4404/pAGS113 was prepared in the same fashion as above for use as a control.

B. Preparation of Plant Material

*N. tabacum* cv. Wisconsin 38 was maintained as an axenic culture on the agar solidified medium MS of Murashige (supra). Apical meristems (1 cm) were excised at 5-7 week intervals, concurrent with the use of the leaf material in protoplast isolation, and placed individually in 3×4 inch Magenta cups containing 50 ml media. The cultures were maintained at 28° C. under "cool white" fluorescent light at 6000 lux, 16 hr/day.

Protoplasts were isolated from expanded leaves. Between 0.5 and 1.0 gm of tissue (fresh weight) was finely divided with a surgical blade in 20 ml of K3 medium (J. I. Nagy et al., *Pflazerphysiol.*, 78, 453-55 (1976)) which contained Cellulase (Cellulysin or Onozuka), 1%; Macerase (Onozuka), 0.1%; Mes buffer (Sigma), 0.1%; and, the elevated phytohormone regime of Caboche (M. Caboche, *Planta*, 149, 7-18 (1980)) at pH 5.6.

Cell wall digestion proceeded overnight (16-18 hours) at 29° C. in darkness with gentle gyrotory shaking (approx. 20 rpm). The digest was poured through a funnel containing four layers of cheesecloth and the cheesecloth was rinsed with K3 media and expressed into Babcock bottles. The bottles were centrifuged 10 minutes at 100 g's. The floating protoplasts were collected with a 1 ml serological pipette, resuspended in a fresh bottle of K3 media and centrifuged again. The protoplasts were collected as before and placed in a known volume of K3 media with glucose (0.4M) replacing sucrose and again the elevated phytohormone regime. The protoplasts were then counted in a hemocytometer and the volume adjusted to provide a final density of $10^5$ protoplast/ml. The protoplasts were cultured in 5 ml aliquots in 100 mm×20 mm "tissue culture treated" petri dishes in darkness at 27° C. for 30 hours prior to cocultivation.

C. Cocultivation of *A. tumefaciens* With Plant Cells

A single bacterial colony of *A. tumefaciens* LBA4404-/pAGS757 prepared as above was suspended in 5 ml minA medium and grown overnight at 27° C. on a roller drum at 40 rpm. An additional 9 hours growth period, after dilution, produced approximately 3 doublings and an appropriate bacterial growth phase/culture density. Microliter amounts of the suspension were then mixed with plant cells prepared as above to yield a multiplicity of 50 bacteria/protoplast (O.D. 550 nm 0.8, corresponding to $10^9$ bacteria/ml). Cocultivation proceeded for 66 hours at 24° C. and 500 lux. Four days after protoplast isolation the cocultivation was terminated by dilution to $2\times10^4$ protoplast equivalents/ml with K3 medium containing cefotaxime (500 ug/ml) and the decreased phytohormone regime of Caboche (M. Caboche, *Planta*, 149, 7-18 (1980)). Thereafter the media was replaced at 3 and 4 day intervals (twice a week) by pelleting the cells by centrifugation at 50-70 g's for 5 minutes. The osmoticum was reduced by 0.05M at each interval by mixing, first, K3 media with an appropriate amount of Media C (J. R. Muller et al., *Physiol. Plant*, 57, 37-41 (1983)) containing sucrose 0.1M, mannitol 0.2M, and later Media C with MS. After three such replacements, cefotaxime could be eliminated from the media without danger of continued bacterial proliferation. This entire procedure was also carried in parallel with *A. tumefaciens* LBA4404/pAGS758 and LBA4404/pAGS759, and with the control *A. tumefaciens* LBA4404/pAGS113.

Transformed plant cells were selected in each of the parallel experiments as follows. Antibiotic resistance in the plant cells was selected by replacing with medium containing kanamycin (50 ug/ml) starting 8 days after protoplast isolation. Transformed calli became visible approximately 21 days after protoplast isolation and the culture density was reduced (4×) to $5\times10^3$ starting protoplast equivalents per ml. At day 25, a further dilution was required to facilitate counting of the transformed calli. At this time the density was reduced (5×) to $10^3$ protoplast equivalent per ml and the medium, MS, was solidified using agarose (Sigma type VII) at a final concentration of 0.25%. Antibiotic resistant calli were counted at day 30.

D. Regeneration of Plants

Regeneration of whole plants was carried out substantially in accordance with the procedures described in P. Zambryski et al., *EMBO J.*, 2, 2143-50 (1983), and in P. Zambryski et al., European Patent Application No. 116,718 (published Aug. 29, 1984). Transformants were potted in soil.

E. Characterization of Transformants

1) Conditional Lethal Phenotype

After potting in soil, the transformants were acclimated to the greenhouse for one week at which time all appeared to be healthy and actively growing. In the first experiment, four plants each from transformations with *A. tumefaciens* LBA4404/pAGS757, LBA4404-/pAGS758, LBA4404/pAGS759 and LBA4404-/pAGS113 were sprayed with a 1 mg/ml solution of naphthalene acetamide (NAM), two plants each, or naphthalene acetic acid (NAA), two plants each, in 20% ethanol, 0.8% Tween 80. Each plant was sprayed to wet completely all upper leaf surfaces (3 to 5 ml per plant). Plants were sprayed within one hour of dusk to minimize evapotranspiration. Four days after spraying, all plants sprayed with NAA showed severe epinasty and had stopped growth; all these plants eventually died. Plants transformed with pAGS113 (control) and sprayed with NAM showed epinasty at the outset, but four days after spraying exhibited reversal of epinasty and resumed growth. The NAM control plants recovered completely. NAM-sprayed plants transformed with pAGS757, pAGS758, or pAGS759 exhibited a range of phenotypes between these two extremes. One of the pAGS757 plants was indistinguishable from the pAGS113 plants, while the other exhibited intermediate sensitivity, recovering five weeks after spraying. Of the two pAGS758 plants, one responded the same as pAGS113 plants, while the other responded the same as an NAA sprayed pAGS113 plant, i.e., exhibited conditional lethality. One pAGS759 plant in this experiment responded exactly as pAGS113 plants; the other displayed weak sensitivity to NAM for nine days, but at nineteen days was indistinguishable from pAGS113 plants.

In a second experiment, two pAGS758 plants were sprayed with NAA; and four pAGS113 plants, two pAGS757 plants, three pAGS758 plants, and one pAGS759 plant were sprayed with NAM. In this experiment, plants had eleven days to acclimate and were larger than in the previous experiment. Consequently, the two NAA sprayed plants showed slightly less sensitivity than in the previous experiment and were still alive, though very weak, at 31 days. The four pAGS113 plants responded similarly to the previous experiment. At 31 days, one pAGS757 and one pAGS758 plant were dead, i.e., responded even more severely than did NAA sprayed plants, one pAGS757 plant was very weak and though not dead was weaker than NAA plants, one pAGS758 plant was slightly sensitive (intermediate between NAA and NAM control plants), and the last pAGS758 and the only pAGS759 plant were equivalent to the pAGS113 plants. Thus it was possible to identify plants, among transformants carrying the iamH gene, that were at least as sensitive to NAM as to NAA. The results of the two experiments are shown in Table I. The numbers in the body of the Table indicate the number of plants having a given response rating (a dash means zero).

TABLE I

| | Response Rating: | | | | |
|---|---|---|---|---|---|
| | 1 | 2 | 3 | 4 | 5 |
| Experiment I | | | | | |
| A. NAA spray | | | | | |
| pAGS 113 | — | — | — | — | 2 |
| 757 | — | — | — | — | 2 |
| 758 | — | — | — | — | 2 |
| 759 | — | — | — | — | 2 |
| B. NAM spray | | | | | |
| pAGS 113 | 2 | — | — | — | — |
| 757 | 1 | — | 1 | — | — |
| 758 | 1 | — | — | — | 1 |
| 759 | 1 | 1 | — | — | — |
| Experiment II | | | | | |
| A. NAA spray | | | | | |
| pAGS 758 | — | — | — | 2 | — |
| B. NAM spray | | | | | |
| pAGS 113 | 4 | — | — | — | — |
| 757 | — | — | — | 1 | 1 |
| 758 | 1 | — | 1 | — | 1 |
| 759 | 1 | — | — | — | — |

Response Ratings:
1 - Minimum effect; full recovery.
2 - Very slight sensitivity; full recovery in two weeks.
3 - Intermediate sensitivity; little or no recovery evident until 4 weeks.
4 - Very sensitive; very weak but alive at 4 weeks.
5 - Maximum sensitivity; dead at 4 weeks.

To recover plants that were maximally sensitive to NAM, plants were decapitated after potting to soil, and after side shoots appeared they were excised and rooted using rooting powder (Rootone). After rooting they were transferred to soil and, after acclimation, sprayed with NAA. The parent plant or one of the cuttings was maintained in order to recover self-cross and backcross seed. For testing response to NAM, rooted cuttings were kept in a growth chamber with high illumination 14 hour days 30° C. C/10 hour nights 20° C. The effect of NAM was less severe in this experiment than in the previous two experiments. Duplicate cuttings were sprayed to control for effects of differential degrees of rooting. Two pAGS757 transformants, four pAGS758 transformants, and two pAGS759 transformants were sprayed in duplicate along with three pAGS113 plants. Two pAGS758 transformants were severely inhibited and not growing at 20 days. Other plants displayed either the same effects as pAGS113 controls (which responded as in previous experiments, only more mildly) or an intermediate effect. Variability in NAM phenotype among individual transformants may be related to variation in the level of expression of the introduced genes in the transformants (e.g., R. Horsch et al., Science, 227, 1229-31 (1985)). Clones of each type were grown to flowering and selfed and backcrossed to obtain progeny. Progeny can be analyzed for heritability of the NAM phenotype and segregation of T-DNA.

2) Segregation Data

Segregation analysis to determine extent to which introduction of the dominant conditional lethal marker in a given transformant is single locus, random and stable can be conducted with plants reproduced (e.g., vegetatively prior to lethality test) from transformants displaying the conditional lethal phenotype. Single locus plants can be used for selection of close-linkage plants, e.g., in accordance with Example 2.

EXAMPLE 4

Introduction of Resistance Conditional Expressive Marker (kanR) into Tobacco

A. Transformation of Plants

Wisconsin 38 tobacco (*Nicotiana tabacum*) protoplasts, prepared as in Example 3, were transformed by cocultivation as in Example 3, but using *A. tumefaciens* strain C58Cl/GV3850kanR of Example 1, to yield transformants which were regenerated as in Example 3.

B. Progeny Testing

The plants so obtained were self-pollinated and backcrossed to Wisconsin 38. Progeny were scored for kanamycin resistance by surface sterilizing, germinating on filter paper in the dark for three days, growing under 500 lux for 1-2 weeks, decapitating shoots in the hypocotyl, and inserting into hormone-free MS solid medium supplemented with kanamycin sulfate (100 mg/l). After growth for two weeks under 5000 lux, resistant plants were clearly distinguishable from sensitive plants: resistant plants formed roots and green leaves, while sensitive plants did not. Results are presented in Table II.

Table II shows actual data and expected data for the self-cross and backcross (to Wisconsin 38) progeny of eighteen transformants (A-R). The actual data were obtained as follows. For each cross, seeds (over 100 in number) were obtained and germinated on moist filter paper. From each group of germinating seeds, 100 plants were selected and decapitated, then inserted into hormone-free MS solid medium supplemented with kanamycin sulfate (100 mg/l). Of the 100 plants for each cross, the number of plants which were kanamycin resistant appears in the "KanR/100" column. (For plant B, 80 rather than 100 plants were measured; the numbers shown for plant B are adjusted to conform to a standard of 100 plants). The expected data show theoretical values for single locus (3:1) and double locus (15:1) insertions of the marker.

As seen from Table II, 14 of the 18 transformants showed segregation data for both self-cross and backcross progeny consistent with single locus insertion. Three of the transformants show data consistent with double locus insertion; one transformant (plant A) fits neither projection. See the column in Table II captioned "#loci." These results show that it is possible to obtain transformed plants in which the introduced gene segregates as a single genetic marker locus.

TABLE II

Segregation of Kanamycin Resistance in *Nicotiana tabacum* Transformed by Cocultivation with pGV3850kanR

| | Self-Cross | | | Backcross | | | |
|---|---|---|---|---|---|---|---|
| | Actual | Expected | | Actual | Expected | | # |
| Plant | KanR/100 | 3:1 | 15:1 | KanR/100 | 1:1 | 3:1 | loci |
| A | 58 | 75 | 93.75 | 38 | 50 | 75 | ? |
| B | 95 | 75 | 93.75 | 72 | 50 | 75 | 2 |
| C | 75 | 75 | 93.75 | 46 | 50 | 75 | 1 |
| D | 94 | 75 | 93.75 | 74 | 50 | 75 | 2 |
| E | 76 | 75 | 93.75 | 48 | 50 | 75 | 1 |
| F | 68 | 75 | 93.75 | 45 | 50 | 75 | 1 |
| G | 93 | 75 | 93.75 | 75 | 50 | 75 | 2 |
| H | 73 | 75 | 93.75 | 45 | 50 | 75 | 1 |
| I | 78 | 75 | 93.75 | 48 | 50 | 75 | 1 |
| J | 73 | 75 | 93.75 | 54 | 50 | 75 | 1 |
| K | 75 | 75 | 93.75 | 51 | 50 | 75 | 1 |
| L | 74 | 75 | 93.75 | 53 | 50 | 75 | 1 |
| M | 81 | 75 | 93.75 | 48 | 50 | 75 | 1 |
| N | 68 | 75 | 93.75 | 50 | 50 | 75 | 1 |
| O | 74 | 75 | 93.75 | 50 | 50 | 75 | 1 |
| P | 72 | 75 | 93.75 | 45 | 50 | 75 | 1 |
| Q | 76 | 75 | 93.75 | 52 | 50 | 75 | 1 |
| R | 72 | 75 | 93.75 | 44 | 50 | 75 | 1 |

What is claimed is:

1. A method of producing a close-linkage dicotyledonous plant containing a marker closely linked to a male sterile locus, comprising:
   a. transforming a first dicotyledonous plant with a marker foreign to the species of said first dicotyledonous plant to produce a group of transformants, said marker being substantially randomly inserted into the genome of the plant and said transforming being carried out by use of Agrobacterium;
   b. selecting a group of single locus transformants from the group of transformants; and
   c. selecting from the group of single locus transformants a close-linkage plant containing a marker in close linkage with a male sterile locus, said close linkage being linkage of less than about 10 recombination units.

2. The method of claim 1 wherein the selecting of a group of single locus transformants comprises selecting by crossing and progeny scoring.

3. The method of claim 1 wherein the selecting of a close-linkage plant comprises selecting by crossing and progeny scoring.

4. The method of claim 1 wherein the marker is an expressive marker.

5. The method of claim 4 wherein the expressive marker is a visible marker.

6. The method of claim 5 wherein the visible marker encodes indigo production.

7. The method of claim 1 wherein the marker is a conditional expressive marker.

8. The method of claim 7 wherein the conditional expressive marker is a chromogenic marker.

9. The method of claim 7 wherein the conditional expressive marker is a resistance marker.

10. The method of claim 9 wherein the resistance marker is a kanamycin resistance marker.

11. The method of claim 7 wherein the conditional expressive marker is a dominant conditional lethal marker.

12. The method of claim 11 wherein the dominant conditional lethal marker is a marker encoding indole acetamide hydrolase.

13. The method of claim 11 wherein the dominant conditional lethal marker is a marker encoding rhizobitoxine synthetase.

14. The method of claim 1 wherein the close linkage is linkage of less than about 5 recombination units.

15. The method of claim 1 wherein the close linkage is linkage of less than about 1 recombination unit.

16. The method of claim 1 wherein the first plant is homozygous for male fertility.

17. The method of claim 1 wherein the first plant is homozygous for male sterility.

18. The method of claim 1 wherein the first plant is heterozygous for male sterility.

19. The method of claim 1 wherein the first plant is selected from the group consisting of cotton, rape, cabbage and tomato.

20. A method of producing hybrid seed in a dicotyledonous plant, comprising:
   a. transforming a first dicotyledonous plant with a marker foreign to the species of said first dicotyledonous plant to produce a group of transformants, said marker being substantially randomly inserted into the genome of the plant and said transforming being carried out by use of Agrobacterium;
   b. selecting a group of single locus transformants from the group of transformants;
   c. selecting from the group of single locus transformants a close-linkage plant containing a marker in close linkage with a male sterile locus, said close linkage being linkage of less than about 10 recombination units;
   d. crossing the close-linkage plant and selecting a close-linkage maintainer line heterozygous for male fertility;
   e. crossing the close-linkage maintainer line with a homozygous male sterile line to yield a mixture of male fertile and male sterile plants;
   f. removing male fertile plants from the mixture based on the presence of the marker to leave a group of plants at least 90% of which are male sterile; and
   g. pollinating said group of plants at least 90% of which are male sterile to yield hybrid seed.

21. The method of claim 20 wherein the selecting of a group of single locus transformants comprises selecting by crossing and progeny scoring.

22. The method of claim 20 wherein the selecting of a close-linkage plant comprises selecting by crossing and progeny scoring.

23. The method of claim 20 wherein the marker is an expressive marker.

24. The method of claim 23 wherein the expressive marker is a visible marker.

25. The method of claim 24 wherein the visible marker encodes indigo production.

26. The method of claim 20 wherein the marker is a conditional expressive marker.

27. The method of claim 26 wherein the conditional expressive marker is a chromogenic marker.

28. The method of claim 26 herein the conditional expressive marker is a resistance marker.

29. The method of claim 28 wherein the resistance marker is a kanamycin resistance marker.

30. The method of claim 26 wherein the conditional expressive marker is a dominant conditional lethal marker.

31. The method of claim 30 wherein the dominant conditional lethal marker is a marker encoding indole acetamide hydrolase.

32. The method of claim 30 wherein the dominant conditional lethal marker is a marker encoding rhizobitoxine synthetase.

33. The method of claim 20 wherein the close linkage is less than about 5 recombination units.

34. The method of claim 20 wherein the close linkage is less than about 1 recombination unit.

35. The method of claim 20 wherein the first plant is homozygous for male fertility.

36. The method of claim 20 wherein the first plant is homozygous for male sterility.

37. The method of claim 20 wherein the first plant is heterozygous for male sterility.

38. The method of claim 20 wherein the first plant is selected from the group consisting of cotton, rape, cabbage and tomato.

39. A close-linkage, dicotyledenous maintainer plant heterozygous for male fertility, said maintainer plant comprising a dominant marker foreign to the species of said maintainer plant closely linked in coupling to a male sterile locus at a linkage of less than about 10 recombination units.

40. A method of producing hybrid seed comprising:
   a. crossing a line of the close-linkage dicotyledenous maintainer plants of claim 39 with a line of homozygous male sterile plants to yield a mixture of male fertile and male sterile plants;
   b. removing male fertile plants from the mixture based on the presence of the marker in said male fertile plants to leave a group of plants at least 90% of which are male sterile; and
   c. pollinating said group of plants at least 90% of which are male sterile to yield hybrid seed.

* * * * *